United States Patent
Kopf et al.

(10) Patent No.: US 9,745,333 B2
(45) Date of Patent: *Aug. 29, 2017

(54) OPTIMIZATION OF SEPARATION FOR VISCOUS SUSPENSIONS

(71) Applicant: SMARTFLOW TECHNOLOGIES, INC., Apex, NC (US)

(72) Inventors: Henry B. Kopf, Cary, NC (US); James A. Kacmar, Apex, NC (US)

(73) Assignee: SMARTFLOW TECHNOLOGIES, INC., Apex, NC (US)

( * ) Notice: Subject to any disclaimer, the term of this patent is extended or adjusted under 35 U.S.C. 154(b) by 463 days.

This patent is subject to a terminal disclaimer.

(21) Appl. No.: 14/448,162

(22) Filed: Jul. 31, 2014

(65) Prior Publication Data
US 2015/0183815 A1    Jul. 2, 2015

Related U.S. Application Data

(63) Continuation of application No. 13/144,967, filed as application No. PCT/US2010/021626 on Jan. 21, 2010, now Pat. No. 8,795,530.
(Continued)

(51) Int. Cl.
*B01D 61/14* (2006.01)
*B01D 61/20* (2006.01)
(Continued)

(52) U.S. Cl.
CPC ............... *C07H 1/08* (2013.01); *B01D 29/56* (2013.01); *B01D 61/145* (2013.01);
(Continued)

(58) Field of Classification Search
CPC ........ C07H 1/08; B01D 29/56; B01D 61/147; B01D 61/58; B01D 63/082; B01D 61/145; B01D 2315/16; B01D 2317/022; B01D 2317/025; B01D 61/142; B01D 2315/10; B01D 61/16; B01D 61/18; B01D 61/20;
(Continued)

(56) References Cited

U.S. PATENT DOCUMENTS 4,420,398 A    12/1983    Castino
4,865,744 A    9/1989    Haertling et al.
(Continued)

FOREIGN PATENT DOCUMENTS

EP         2133135        12/2009
WO    WO 2008/123099    10/2008

*Primary Examiner* — Joseph Drodge
(74) *Attorney, Agent, or Firm* — Tristan Fuierer; Marianne Fuierer; Moore & Van Allen, PLLC

(57) ABSTRACT

The present invention relates to methods and systems for optimization of dilution of a viscous starting material to isolate and/or concentrate the product of interest from the starting source material such that the process minimizes the volume of diluent and the total volume of the waste stream generated during the process as well as maximizing the yield of desired product. The system employs cross-flow filtration modules with sub-channels that are equidistant to the inlet and outlet of said modules and such modules are characterized by optimal channel height, optimal transmembrane pressure, etc., which are selected in order to achieve the best combination of product quality and production yield.

6 Claims, 12 Drawing Sheets

Related U.S. Application Data

(60) Provisional application No. 61/146,142, filed on Jan. 21, 2009, provisional application No. 61/148,959, filed on Jan. 31, 2009.

(51) Int. Cl.
  *C07H 1/08* (2006.01)
  *C12M 3/06* (2006.01)
  *B01D 61/58* (2006.01)
  *B01D 63/08* (2006.01)
  *B01D 29/56* (2006.01)

(52) U.S. Cl.
  CPC ........... *B01D 61/147* (2013.01); *B01D 61/58* (2013.01); *B01D 63/082* (2013.01); *B01D 61/142* (2013.01); *B01D 2315/10* (2013.01); *B01D 2315/16* (2013.01); *B01D 2317/022* (2013.01); *B01D 2317/025* (2013.01)

(58) Field of Classification Search
  CPC ............ B01D 2311/08; B01D 2311/04; B01D 2311/2688; B01D 2316/16; C12M 1/12; C12M 1/123; C12M 1/125; C12M 1/126; C12M 3/06; C12M 3/062; C12M 3/065; C12N 1/00
  USPC ...... 210/137, 201, 202, 195.2, 257.2, 321.6, 210/321.72, 321.75, 321.84, 637, 641, 210/650–654, 805; 422/534; 435/41, 435/70.3, 71.1, 239, 383, 384, 401, 308.1
  See application file for complete search history.

(56) References Cited

U.S. PATENT DOCUMENTS

| | | |
|---|---|---|
| 4,867,876 A | 9/1989 | Kopf |
| 4,882,050 A | 11/1989 | Kopf |
| 4,956,085 A | 9/1990 | Kopf |
| 5,034,124 A | 7/1991 | Kopf |
| 5,049,268 A | 9/1991 | Kopf |
| D322,117 S | 12/1991 | Kopf |
| D323,202 S | 1/1992 | Kopf |
| D324,720 S | 3/1992 | Kopf |
| D325,070 S | 3/1992 | Kopf |
| D327,313 S | 6/1992 | Kopf |
| D328,789 S | 8/1992 | Kopf |
| 5,232,589 A | 8/1993 | Kopf |
| 5,342,517 A | 8/1994 | Kopf |
| 5,356,639 A | 10/1994 | Jameson et al. |
| D357,059 S | 4/1995 | Kopf |
| 5,593,580 A | 1/1997 | Kopf |
| 5,597,486 A | 1/1997 | Lutz |
| 5,618,432 A * | 4/1997 | Rewitzer ............... B01D 3/143 134/10 |
| 5,868,930 A | 2/1999 | Kopf |
| 6,022,742 A | 2/2000 | Kopf |
| 6,048,727 A | 4/2000 | Kopf |
| 6,139,746 A | 10/2000 | Kopf |
| 6,214,221 B1 | 4/2001 | Kopf |
| 6,214,574 B1 | 4/2001 | Kopf |
| 6,383,380 B1 | 5/2002 | Kopf |
| 6,569,340 B2 | 5/2003 | Kopf et al. |
| 6,596,172 B1 | 7/2003 | Kopf |
| 6,827,960 B2 | 12/2004 | Kopf et al. |
| 6,852,352 B2 | 2/2005 | Kopf et al. |
| 6,875,459 B2 | 4/2005 | Kopf et al. |
| 6,946,075 B2 | 9/2005 | Kopf |
| 7,141,171 B2 | 11/2006 | Lightfoot, Jr. |
| 7,384,549 B2 | 6/2008 | de los Reyes et al. |
| 7,544,296 B2 | 6/2009 | Kopf et al. |
| 8,152,999 B2 | 4/2012 | Lightfoot, Jr. |
| 8,795,530 B2 * | 8/2014 | Kopf .................... B01D 61/145 210/639 |
| 9,163,265 B2 * | 10/2015 | Benson ................. C10G 31/09 |
| 2005/0023194 A1 | 2/2005 | Petersen et al. |
| 2005/0100635 A1 * | 5/2005 | Firary ...................... A23L 2/04 426/53 |
| 2006/0051347 A1 * | 3/2006 | Winter ............. A61K 39/39591 424/133.1 |
| 2006/0110399 A1 | 5/2006 | Van Holten et al. |
| 2006/0194313 A1 * | 8/2006 | Pierce .................... B01D 61/16 435/325 |
| 2007/0163628 A1 | 7/2007 | Zimmer |
| 2007/0237762 A1 | 10/2007 | Winter |
| 2007/0246406 A1 | 10/2007 | Dibel et al. |
| 2008/0017576 A1 | 1/2008 | Belfort et al. |
| 2009/0277833 A1 | 11/2009 | Mir et al. |
| 2011/0195462 A1 * | 8/2011 | Banks ................. C12M 21/14 435/101 |
| 2014/0066359 A1 | 3/2014 | Carlsson |

\* cited by examiner

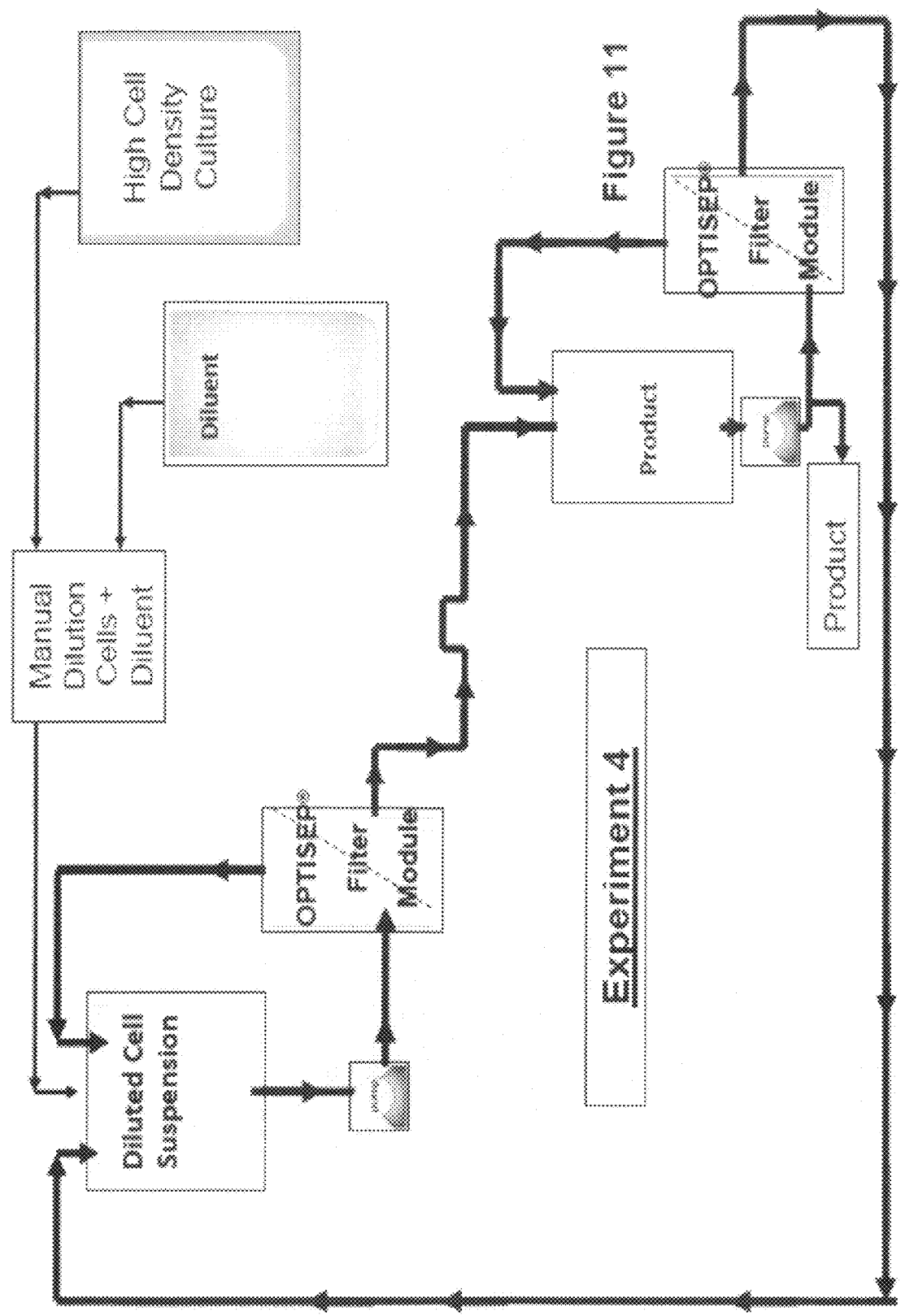

OPTIMIZATION OF SEPARATION FOR VISCOUS SUSPENSIONS

CROSS-REFERENCE TO RELATED APPLICATIONS

This application is a continuation application of co-pending U.S. patent application Ser. No. 13/144,967 filed on Sep. 6, 2011 and now U.S. Pat. No. 8,795,530 which was filed under the provisions of 35 U.S.C. §371 and claimed priority of International Patent Application No. PCT/US2010/021626 filed on Jan. 21, 2010, which in turn claimed priority to U.S. Provisional Patent Application Ser. No. 61/146,142 filed on Jan. 21, 2009 and U.S. Provisional Patent Application Ser. No. 61/148,959, filed on Jan. 31, 2009, the contents of which are incorporated herein by reference in their entirety.

BACKGROUND OF THE INVENTION

Field of Invention

The present invention relates to separation of viscous source materials, and more particularly, to methods and systems for optimization of dilution of a viscous starting material to isolate and/or concentrate the product of interest from the starting source material such that the process minimizes the volume of diluent and the total volume of the waste stream generated as well as maximizing the yield of desired product.

Discussion of Related Technology

Throughout the world more and more companies are looking to recover value added products from a wide variety of starting materials including plants, roots, root crops, grains, flowers, animal tissue, cell cultures comprising yeast, algal, bacteria, or fungi species, milk, milk products, fruits and fruit juices. Additional companies are looking to extract value added products from solid and liquid waste streams such as mill and grain wash waters and fermentation biomass. One such waste stream will be the bio-mass from bio-fuel production which after production of fuels such as diesel and alcohol will still be rich in plant proteins, sugars and carbohydrates. Another such waste stream will be cellular bio-mass used for protein and essential fatty acids production from wild and/or recombinant yeast, algae, bacteria, larvae or fungi species.

A common practice for dry or solid starting materials is to solubilize starting materials in a solvent such as aqueous and organic solvents so that the valuable component becomes soluble in the solvent. The solution is then processed by one or more of the known techniques of filtration, precipitation, extraction, chromatography and centrifugation to separate the valuable components from the starting material and solvent. As a result of growth in demand for naturally derived products companies are increasing production of these products. Production costs and environmental issues such as the release of contaminated liquid waste streams have pressured companies to extract more of the final product from the starting material and to minimize the use of solvents by preparing larger more viscous process streams.

In recent years the science of cell culture has also endeavored to increase production of cell derived products such as antibiotics, vaccine and therapeutic compounds by increasing the density of the cell cultures utilized to produce these highly valuable materials. Increased cell density can be a highly beneficial as it allows for the increased production of the final product in the same space as a less dense cell culture. It would seem that doubling the concentration of a cell culture forming a viscous material should yield twice as much final product without any substantial increase in fermentation facility costs.

However, it has been found that all of these highly viscous materials are far more difficult to process, such that, even though the cell culture is five (5) times denser the yield of final product is only 50% greater because the viscosity of the material prevents the separation of the desired target molecule from the mass of cellular materials. In the case of extracts of solid phase material such as plants and animal tissue the problem is the same such that the viscous materials clog filters and block chromatography columns as well as not separating efficiently under normal centrifugal forces. One way of describing the problem is to say that although larger crowds would contain more people able to buy a particular good or service it is harder to get the people with money through the stores doors due to the congestion caused by the crowd itself.

Although it would appear that a simple dilution of the viscous material would solve the problem, this creates at least four additional problems: 1) the cost of the diluent which can be highly expensive in the case of diluents for pharmaceutical intended for human injection, 2) disposal of the higher volume of the waste stream, i.e. the original volume plus the volume of diluent, 3) the cost of the necessary tanks and mixing equipment in order to dilute the starting material, and 4) additional purification costs for the diluted final product.

As important as these problems are the single most important point is to have the highest percentage of yield so that the initial purpose of processing higher density materials is not negated by problems with recovery of the desired product. Thus, it would be advantageous to provide a method and system that provides higher yields from high density materials.

SUMMARY OF THE INVENTION

The present invention solves all of the aforementioned problems in a simple, inline, space efficient and continuous process that lowers costs and maximizes yield.

The present invention relates to the method and apparatus necessary to dilute a viscous starting material to isolate and/or concentrate the product of interest from the starting material such that the process minimizes the volume of diluent and the total volume of the waste stream generated as well as maximizing the yield of desired product.

One such method employs one or more cross-flow filter units and their associated pumps, pipes and tanks. It is also a further embodiment of this invention that the further purification of the target of interest can be accomplished by complimentary purification techniques such as chromatography all as one unit of operation.

An extremely beneficial element of this method is that the process can be readily modeled and optimized on the laboratory scale, with volumes as small as 0.5 L or in a continuous flow of 1 liter per minute for example. This is extremely important in the pharmaceutical market as large volumes of highly specific therapeutic proteins are neither inexpensive nor readily available. The separation methods of the present invention are envisioned in batch mode, continuous, or semi continuous mode.

One aspect of the present invention relates to a process for purifying one or more target substances from a viscous source material, the process comprising:

contacting the viscous source material with a diluent in an amount sufficient to reduce the viscosity of the viscous source material and form a continuous stream of diluted source material, wherein the diluent is contained in a separated vessel from the viscous source material;

flowing the diluted source material into a recirculation loop of a first cross-flow filter apparatus;

diafiltering the diluted source material with sufficient diafiltration buffer so as to recover the desired yield of the target substance by passing said target substance into the first permeate fluid;

flowing the first permeate fluid containing the target substance to a end product vessel;

flowing out the first retentate solution from the recirculating liquid of the first cross-flow filter into a second cross-flow filter unit, wherein the flow rate of the first retentate solution is at the same flow rate as the diluted source material being fed into the recirculation loop of the first cross-flow filter apparatus;

diafiltering the flow of retentate into the second cross-flow filter unit with sufficient diafiltration buffer so as to recover the desired yield of the target substance by passing said target substance into the second permeate fluid;

flowing the second permeate fluid containing the target substance to the end product vessel;

concentrating the first and second retentate fluid by flowing same to a third cross-flow filter apparatus communicatively connected with the second cross-flow filter unit, wherein the volume of the third retentate fluid is reduced to the approximate volume of the undiluted source material or less thereby forming a waste stream for further use;

recirculating the third permeate fluid back to the diluent vessel for reuse;

concentrating the first and second permeate fluid by flowing same to a fourth cross-flow filter apparatus communicatively connected to the end product vessel wherein target substance is concentrated and diafiltration buffer is removed in fourth permeate stream and recirculated for reuse.

In another aspect, the present invention provides for a method of for separating a target substance, the method comprising:

providing a diluent to a first reservoir;
providing a starting source material to a second reservoir:
providing a buffer to a third reservoir;
flowing a portion of the starting material with a portion of diluent to form a mixture and flowing the mixture to a first cross-flow filtration apparatus;
recirculating the mixture of diluent and starting material in the first cross-flow filtration apparatus in a flow path adapted for:
diafiltering the mixture;
permeating the target substance through the membrane;
selectively flowing a portion of the retentate of the first cross-flow filtration apparatus to a second cross-flow filtration apparatus;
recirculating the retentate of the first cross-flow filtration apparatus across to a second cross-flow filtration apparatus in a flow path adapted for:
selectively flowing a portion of the retentate out of the second cross-flow filtration apparatus as a concentrate;
selectively flowing the permeate to a product reservoir; and capturing the permeate of the first cross-flow filtration apparatus in the product reservoir.

Optionally, the permeate fluid of the first cross-flow filtration apparatus in the product reservoir can be recirculated across a third cross-flow filtration apparatus in a flow path adapted for:
concentrating the molecule of interest in the product reservoir;
permeating the target substance free liquid into the third reservoir;
selectively flowing the liquid in the third reservoir into the first cross-flow filtration apparatus as the diafiltration buffer.

In a still further aspect, the present invention provides for a system comprising:

a first reservoir constructed and arranged for holding a diluent solution, and for selectively flowing liquid into and out of said first reservoir;

a second reservoir constructed and arranged for holding a starting material, and for selectively flowing liquid into and out of said second reservoir, the second reservoir can be the cell culture reservoir such as a fermentor or culture bag;

a first cross-flow filtration apparatus for separating liquids into permeate and retentate streams, provided with means for flowing liquid in and permeate and retentate streams out of said first cross-flow filtration apparatus;

a second cross-flow filtration apparatus for separating liquids into permeate and retentate streams, provided with means for flowing liquid in and permeate and retentate streams out of said second cross-flow filtration apparatus;

a third reservoir constructed and arranged for holding a buffer, and for selectively flowing liquid into and out of said third reservoir;

a third cross-flow filtration apparatus for separating liquids into permeate and retentate streams, provided with means for flowing liquid in and permeate and retentate streams out of said third cross-flow filtration apparatus;

a product reservoir constructed and arranged for holding the isolated product, and for selectively flowing liquid into and out of said fourth reservoir; and conduit, valve and pump means constructed and arranged for:
providing an initial volume of diluent to the first reservoir;
providing an initial volume of buffer to the third reservoir;
selectively flowing a portion of the starting material with a portion of diluent to form a mixture and flowing the mixture to the first cross-flow filtration apparatus;
recirculating the mixture of diluent and starting material in the first cross-flow filtration apparatus in a flow path adapted for:
diafiltering the mixture;
permeating the target substance through the membrane;
selectively flowing a portion of the retentate of the first cross-flow filtration apparatus to the second cross-flow filtration apparatus;
recirculating the retentate of the first cross-flow filtration apparatus across the second cross-flow filtration apparatus in a flow path adapted for:
selectively flowing a portion of the retentate out of the second cross-flow; filtration apparatus as a concentrate;
selectively flowing the permeate to the first reservoir;
capturing the permeate of the first cross-flow filtration apparatus in the product reservoir and recirculating the permeate fluid of the first cross-flow filtration apparatus in the product reservoir across the third cross-flow filtration apparatus in a flow path adapted for:

concentrating the molecule of interest in the product reservoir;

permeating the target substance free liquid into the third reservoir;

selectively flowing the liquid in the third reservoir into the first cross-flow filtration apparatus as the diafiltration buffer.

Yet another aspect of the invention provides for a process for isolation of a desirable product from a viscous starting mixture; the process comprising the steps of:

diluting the starting mixture with a minimum amount of diluent necessary for effecting passage of the target substance through a first cross-flow filter membrane;

continually diafiltering the diluted material on the first cross-flow filter membrane with sufficient diafiltration volumes of buffer to achieve the desired yield of product in the permeate; and concentrating the permeate on a second cross-flow filter membrane to recover the diluent for recycling while simultaneously concentrating the permeate fluid containing the product of interest on the second cross-flow filter membrane, such that the product is concentrated.

Importantly, the product-free permeate is utilized and recycled as the diafiltration buffer such that at the end of the process, the product has been isolated from the viscous starting mixture and concentrated into a smaller volume, i.e. less than the volume of the undiluted starting material. Further any remaining starting material is returned to the initial undiluted viscous volume, or a lower volume, and no buffers where consumed other than the initial volumes utilized to start the process.

The present system and method may be carried out to effect a separation selected from the group consisting of: separating insect cell culture fluid into its constituent parts; separating viral culture fluid into its constituent parts; separating an immunoglobulin from an immunoglobulin-containing culture of bacteria, yeast, algal, fungus, insect cells, or animal cells; separating an immunoglobulin from serum; separating a clotting factor from a clotting factor-containing culture of bacteria, yeast, fungus, insect cells, or animal cells; separating a protein from a protein-containing culture of bacteria, yeast, fungus, insect cells, or animal cells; separating an antigen from an antigen-containing culture of bacteria, yeast, fungus, insect cells, or animal cells; separating an antigen from a viral culture containing same; separating a hormone from a hormone-containing culture of bacteria, yeast, fungus, insect cells, or animal cells; separating essential fatty acids from a fatty acid containing culture of bacteria, yeast, algal, fungus, insect cells, larva or animal cells; separating a glycoprotein from a viral culture; and/or separating a glycoprotein from a glycoprotein-containing culture of bacteria, yeast, fungus, insect cells, or animal cells.

Other aspects and advantages of the invention will be more fully apparent from the ensuing disclosure and appended claims.

BRIEF DESCRIPTION OF THE FIGURES

FIG. 11 shows the component necessary to separate the product from cells by constant volume diafiltration while simultaneously concentrating the product.

DETAILED DESCRIPTION OF THE INVENTION

In the description of the present invention, certain terms are used as defined below.

A "source material or starting material" as used herein refers to a viscous mixture containing solid and liquid materials such as mill and grain wash waters, culture medium and fermentation bio-mass. The source or substance material are often complex mixtures or solutions containing many biological molecules such as proteins, antibodies, essential fatty acids, hormones, and viruses as well as small molecules such as salts, sugars, lipids, etc. Examples of source or substance material that may contain valuable biological substances amenable to the purification method of the invention include, but are not limited to, a culture supernatant from a bioreactor, a homogenized cell suspension, plasma, plasma fractions, milk, colostrum and cheese whey.

"Essential fatty acids (EFAs)," as used herein, means Omega-3 Fatty Acids and Omega-6 Fatty Acid. EFAs are given the title 'essential' not only because they are critical in promoting overall health, but because they cannot be manufactured by the body; therefore, it is essential that intake is through diet. EFAs are considered to be long chain polyunsaturated fatty acids (PUFAs). PUFAs of importance include, but are not limited to, docosahexaenoic acid (DHA), eicosapentaenoic acid (EPA), alpha-linolenic acid (ALA), gamma-linolenic acid (GLA), docosapentaenoic acid (DPA), arachidonic acid (all-cis-5,8,11,14-eicosatetraenoic acid; AA) and stearidonic acid (cis-6,9,12,15-octadecatetraenoic acid; SDA).

"Cross-flow filtration module" refers herein to a type of filter module or filter cassette that comprises a porous filter element across a surface of which the liquid medium to be filtered is flowed in a tangential flow fashion, for permeation through the filter element of selected component(s) of the liquid medium and include hollow fibers, spiral wound nodules, ceramic filters, cassette filters, plate and frame filters etc.

In a cross-flow filtration module employed in the present invention, the shear force exerted on the filter element (separation membrane surface) by the flow of the liquid medium serves to oppose accumulation of solids on the surface of the filter element. Useful cross-flow filters include microfiltration, ultrafiltration, nanofiltration and reverse osmosis filter systems. The cross-flow filters can be used in parallel or series flow path stacked in a single housing or multi-element housing arranged as a single or multiple loop system.

Figure 2:
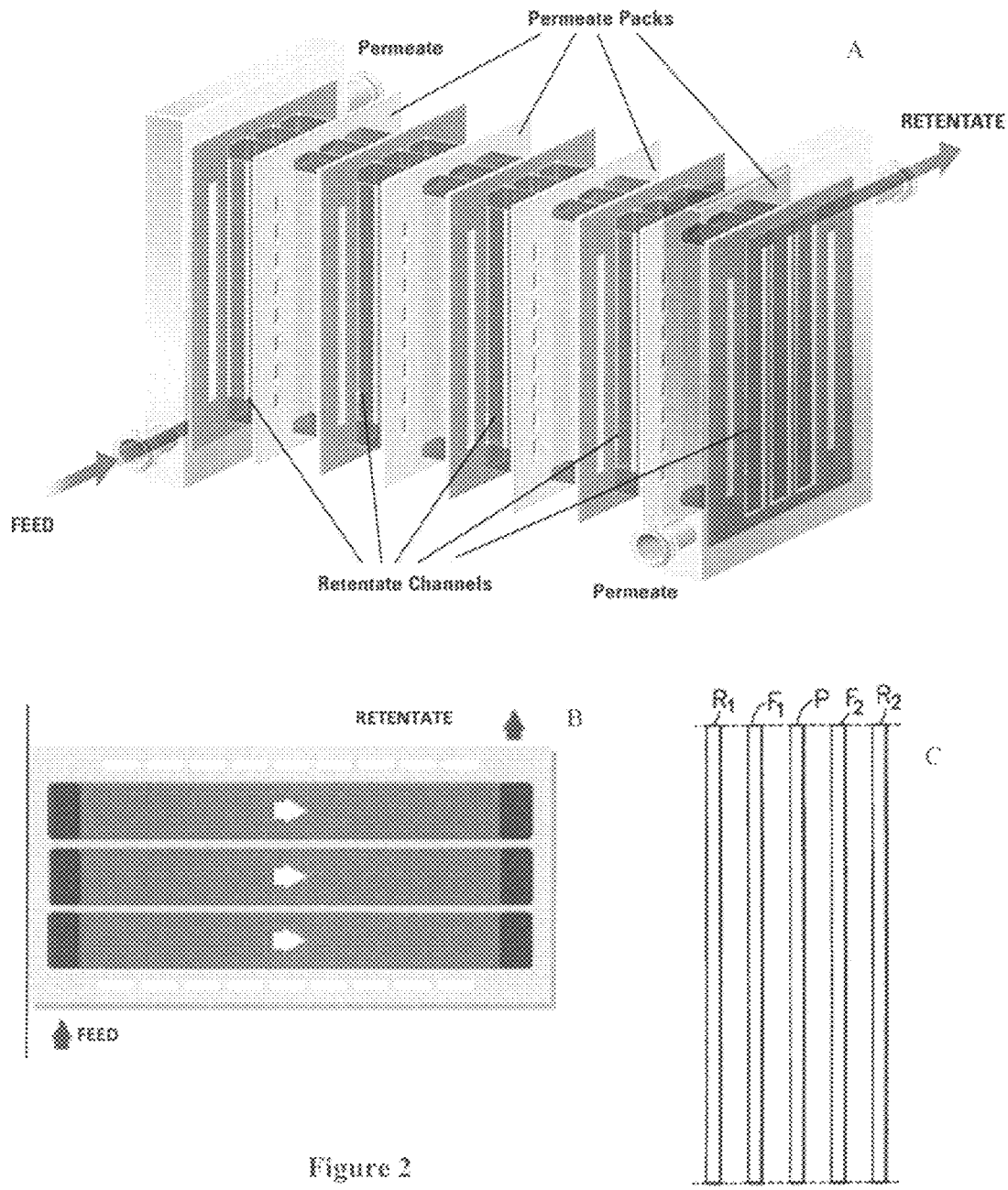

A preferred cross-flow filter system comprises a multiplicity of filter sheets (filtration membranes) in an operative stacked arrangement, e.g., wherein filter sheets alternate with permeate and retentate sheets, and as a liquid to be filtered flows across the filter sheets, impermeate (non-permeating) species, e.g., solids or high-molecular-weight species of diameter larger than the filter sheet's pore size(s), are retained and enter the retentate flow, and the liquid along with any permeate species diffuse through the filter sheet and enter the permeate flow (See FIG. 2 B). In a preferred embodiment of the present invention, such cross-flow filtration module comprises a permeate collection and discharge arrangement, a feed inlet, a retentate outlet, and multiple fluid-flow sub-channels that may for example be equidistant to the inlet and the outlet as shown in FIGS. 2 A and C.

Cross-flow filtration modules and cross-flow filter cassettes useful in practice of the present invention are commercially available from Smartflow Technologies Inc, (Cary, N.C.), and are variously described in the following United States patents: U.S. Pat. No. 4,867,876, "Filter Plate, Filter Plate Element, and Filter Comprising Same, issued Sep. 19, 1989; U.S. Pat. No. 4,882,050, same title, issued Nov. 21, 1989; U.S. Pat. No. 5,034,124, same title, issued Sep. 11, 1990; U.S. Pat. No. 5,049,268, same title, issued Sep. 17, 1991; U.S. Pat. No. 5,232,589, "Filter Element and Support, issued Aug. 3, 1993; U.S. Pat. No. 5,342,517, "Filter Cassette Article," issued Aug. 30, 1994; U.S. Pat. No. 5,593,580, same title, issued Jan. 14, 1997; and U.S. Pat. No. 5,868,930, same title, issued Feb. 9, 1999; the disclosures of all of which are hereby incorporated herein by reference in their respective entireties.

Briefly, a preferred cross-flow filter cassette of the present invention is a stacked cassette filter assembly, as shown in FIG. 2A, in which the base sequence of retentate sheet (R), filter sheet (F), permeate sheet (P), filter sheet (F), and retentate sheet (R) may be repeated in the sequence of sheets in the filter assembly as desired, e.g., in a repetitive sequence of retentate sheet (R), filter sheet (F), retentate sheet (R), filter sheet (F), permeate sheet (P), filter sheet (F), retentate sheet (R), filter sheet (F), permeate sheet (P), filter sheet (F), retentate sheet (R), filter sheet (F), retentate sheet (R). Thus, the filter cassette of a desired total mass transfer area is readily formed from a stack of the repetitive sequences. In all repetitive sequences, except for a single unit sequence, the following relationship is observed: where X is the number of filter sheets, 0.5 X−1 is the number of interior retentate sheets, and 0.5X is the number of permeate sheets, with two outer retentate sheets being provided at the outer extremities of the stacked sheet array.

The filter sheets, and the retentate and permeate sheets employed therewith, may be formed of any suitable materials of construction, including, for example, polymers, such as polypropylene, polyethylene, polysulfone, polyethersulfone, polyetherimide, polyimide, polyvinylchloride, polyester, etc.; nylon, silicone, urethane, regenerated cellulose, polycarbonate, cellulose acetate, cellulose triacetate, cellulose nitrate, mixed esters of cellulose, etc.; ceramics, e.g., oxides of silicon, zirconium, and/or aluminum; metals such as stainless steel; polymeric fluorocarbons such as polytetrafluoroethylene; and compatible alloys, mixtures and composites of such materials.

Preferably, the filter sheets, retentate and permeate sheets are made of materials which are adapted to accommodate high temperatures and chemical sterilants, so that the interior surfaces of the filter may be steam sterilized and/or chemically sanitized for regeneration and reuse, as "steam-in-place" and/or "sterilizable in situ" structures, respectively. Steam sterilization typically may be carried out at temperatures on the order of from about 121° C. to about 130° C., at steam pressures of 15-30 psi, and at a sterilization exposure time typically on the order of from about 15 minutes to about 2 hours, or even longer. Alternatively, the entire cassette structure may be formed of materials which render the cassette article disposable in character.

In one particular aspect, the present invention relates to a filtration cassette comprising a multilaminate array of sheet members of generally rectangular and generally planar shape with main top and bottom surfaces, wherein the sheet members include in sequence in the array a first retentate sheet, a first filter sheet, a permeate sheet, and second filter sheet, and a second retentate sheet, wherein each of the sheet members in the array has at least one inlet basin opening at one end thereof, and at least one outlet base opening at an opposite end thereof, with at least one permeate passage opening at longitudinal side margin portions of the sheet members;

each of the first and second retentate sheets having at least one channel opening therein, wherein each channel opening extends longitudinally between the inlet and outlet basin openings of the sheets in the array and is open through the entire thickness of the retentate sheet, and with each of the first and second retentate sheets being bonded to an adjacent filter sheet about peripheral and side portions thereof, with their basin openings and permeate passage openings and register with one another, and arranged to permit flow of filtrate through the channel openings of the retentate sheet between the inlet and outlet basin openings to permit permeate flow through the filter sheet to the permeate sheet to the permeate passage openings;

the filtration cassette comprising a unitary article of inter-bonded sheet members.

In another embodiment, the present invention relates to a filtration cassette comprising a multilaminate array of sheet members of generally rectangular and generally planar shape with main top and bottom surfaces, wherein the sheet members include in sequence in said array a first retentate sheet, a first filter sheet, a permeate sheet, a second filter sheet, and a second retentate sheet, wherein each of the sheet members in said array has at least one inlet basin opening at one end thereof, and at least one outlet basin opening at an opposite end thereof, with at least one permeate passage opening at a longitudinal side margin portion of the sheet members;

each of the first and second retentate sheets having at least one channel opening therein, extending longitudinally between the inlet and outlet basin openings of the sheets in the array, and being bonded (e.g., compression bonded) to an adjacent filter sheet about peripheral end and side portions thereof, with their basin openings and permeate passage openings in register with one another and the filtrate passage openings of each of the retentate sheets being circumscribingly bonded to the adjacent filter sheet, and with a central portion of each of the retentate sheets and adjacent filter sheets being unbonded to permit permeate contacting the retentate sheet to flow through the filter sheet to the permeate sheet; and each of the filter sheets being secured at its peripheral portions on a face thereof opposite the retentate sheet, to the permeate sheet.

In yet another embodiment, the present invention relates to a filtration cassette comprising a multilaminate array of sheet members of generally rectangular and generally planar shape with main top and bottom surfaces, wherein the sheet members include:

a first retentate sheet of suitable material, e.g. polysulfone, polyethersulfone, polycarbonate, urethane, silicone, or other material of construction, having (i) at least one longitudinally extending rib or partition element, such partition element(s) when provided in multiple configuration being transversely spaced-apart from one another and being of substantially the same height and substantially parallel to one another to define a single or a series of channels between the partitions, extending longitudinally between the respective inlet and outlet basin openings of associated filter elements and permeate sheet members, on both faces thereof, (ii) filtrate passage openings at side portions of the sheets, and (iii) the retentate sheet aligned to the first sheet of filter material at respective end and side portions thereof, with the basin openings and filtrate passage openings of the associated sheet members in register with one another and the filtrate passage opening of the retentate sheet member being circumscribingly compressed against the first sheet of filter material, and with a central portion of the first sheet of filter material and the retentate sheet member being unbonded to permit permeate contacting the retentate sheet member to flow through the first sheet member of filter material to the permeate sheet member;

a first sheet member of filter material having (i) at least one basin opening, of a suitable shape, e.g., polygonal, semicircular, oval or sector shape, at each of opposite end portions of the sheet member defining respective inlet and outlet passages, and (ii) at least one filtrate passage opening at the side portions of the sheet member, wherein the first sheet member of filter material is bonded to the permeate sheet member at their respective end and side portions, with their basin openings and filtrate passage openings in register with one another and the basin openings being circumscribingly bonded at respective end portions of the first sheet member of filter material and the permeate sheet member, and with a central portion of the first sheet member of filter material and the permeate sheet member being unbonded so as to define a central portion permeate channel of the permeate sheet communicating with the filtrate passages in the first sheet member of filter material and in the permeate sheet member;

a permeate sheet member, having (i) multiple basin openings of suitable shape at each of opposite end portions of the sheet member defining respective inlet and outlet passages, and (ii) filtrate passage openings at the side portions of the sheet member;

a second sheet member of filter material having (i) at least one basin opening at each of opposite end portions of the sheet member defining respective inlet and outlet passages, and (ii) at least one filtrate passage opening at the side portions of the sheet member, wherein the second sheet member of filter material is compression sealed to the retentate sheet member at their respective end and side portions, with their basin openings and filtrate passage openings in register with one another and the filtrate passage opening of the retentate sheet member being compression sealed to the second sheet member of filter material, and with a central portion of the second sheet member of filter material and the retentate sheet member being unbonded to permit permeate contacting the retentate sheet member to flow through the second sheet member of filter material; and a second retentate sheet member of suitable material, e.g. polysulfone, polyethersulfone, polycarbonate, urethane, silicone, having (i) at least one longitudinally extending rib or partition element, provided that when multiple partition elements are employed, the partition elements are transversely spaced-apart from one another, such partition elements being of substantially the same height and substantially parallel to one another, to define a single channel or a series of channels between the partitions, extending longitudinally between the respective inlet and outlet basin openings of the filter elements and permeate sheet members, on both faces thereof, (ii) filtrate passage openings at the side portions of the sheet member, and (iii) the retentate sheet compression sealed to the second sheet of filter material at respective end and side portions thereof, with their basin openings and filtrate passage openings in register with one another and the filtrate passage opening of the retentate sheet member being compression sealed to the second sheet member of filter material, and with a central portion of the first sheet member of filter material and the retentate sheet member being unbonded to permit permeate contacting the retentate sheet member to flow through the second sheet member of filter material to the permeate sheet member.

The end plates used with the cassette articles of the invention to form a unitary filter assembly may be formed of any suitable materials of construction, including, for example, stainless steel or other suitable metal, or polymers such as polypropylene, polysulfone, and polyetherimide.

Specifically, the present invention employs cross-flow filtration modules with sub-channels that are equidistant to the inlet and outlet of said modules such as shown in FIGS. 2A and 2C (retentate sheet). Moreover, said cross-flow filtration modules are characterized by optimal channel height, optimal transmembrane pressure, optimal membrane pore size and pore structure, optimal membrane chemistry, etc., which are selected in order to achieve the best combination of product quality and production yield.

For example, shear at the surface of the membrane is critical in minimizing gel layer formation, but excessive shear is deleterious in the following three key aspects: (1) excessive shear increases energy consumption, (2) excess shear interferes with diffusion at the membrane surface, upon which separation process directly depends, (3) excessive shear can deprive certain compounds of their bioactivities. It is therefore desirable to maintain shear within an optimal range.

Furthermore, it is possible to optimize the separate processes with cross-flow filtration modules of variable channel velocities but of uniform channel heights, given the fact that most commercial cross-flow modules are only available in a single channel height. When the channel height of a cross-flow filtration module is known, shear is directly proportional to channel velocity of such module for the same solution passing by.

In the literature, numerous techniques have been proposed to effect the separation of target substances using membrane separations with addition of foreign substances such as acid, base, salt and solvents. In contrast to these chemical additives-based methods, the methodology of the present invention permits a target substance to be separated from an input fluid by the simplest mechanical means. In the use of cross-flow filtration modules of the type described in the aforementioned patents, the specificity and speed of a desired separation is effected by a) fluid distribution in the cross-flow module, b) channel height of the cross flow module, c) channel length, d) shear rate, e) membrane pore structure, f) membrane structure, g) membrane chemistry, h) trans-membrane pressure, and i) pressure drop, which is a function of channel length, velocity and solution viscosity.

The approaches by others involving various additives and manipulations of transmembrane pressure appear to be predicated on overcoming problems created by poor distribution of flow within the cross-flow module. It is not to say that the addition of salts and solvents do not have a place in separation but without proper flow distribution the membrane separation cannot be optimally operated nor will cleaning techniques be fully beneficial. It will be appreciated, based on the disclosure herein that numerous heretofore expensive or difficult separations are rendered far simpler and more economical by employing the techniques described herein.

Thus, the invention relates in another aspect to optimizing the membrane separation process, comprising:

selecting a cross-flow membrane module wherein the distance from the inlet port to the outlet port is equidistant from the inlet to outlet for each sub-channel of the device, i.e., each sub-channel is of a same dimensional character;
selecting an optimal channel height;
selecting an optimal shear rate and/or channel velocity;
selecting an optimal transmembrane pressure;
selecting an optimal membrane pore size;
selecting an optimal temperature;
selecting an optimal channel length; and
selecting an optimal pressure drop which is the composite of
  the optimal channel height;
  the optimal shear rate and/or channel velocity;
  optimal channel length; and
  the viscosity of the solution being filtered.

Selecting a channel height can be performed mathematically or empirically by trial and error. In most cell fermentation applications, trial and error has been more appropriate due to the fact that the viscosity of the cell broth or product solution is rarely known, the cell count and cell viability are highly variable, and the solution is frequently non-Newtonian. The objective of channel selection is to minimize channel height with three critical stipulations: first, the channel must be sufficiently high to allow the unrestricted passage of any larger material such as clumped cells; second, the channel should not cause excessive pressure drop and loss of linear efficiency; and third, the channel should be sufficiently high as to allow the proper angle of attack for substances to encounter the membrane pore and pass through the pore. The optimal channel height is dependent on the length and viscosity of the solution.

Several notable observations have been made in initial trials and process scale-up, as discussed below.

For cell suspensions having an optical density (OD) of 2 to 500, and a path length of 6 to 12 inches, start with a channel height between 0.4 to 0.75 mm. If the inlet pressure is above 15 PSIG at a velocity of 2.0 M/sec, then the channel is too thin.

For cell suspensions having an optical density (OD) of 2 to 500, and a path length of 6 to 12 inches, start with a channel height between 0.4 to 0.75 mm. If the inlet pressure is below 5 PSIG at a velocity of 2.0 M/sec the channel is too high.

For cell suspensions having an optical density (OD) of 2 to 500, and a path length of 25 to 40 inches, start with a channel height between 0.7 to 1.0 mm. If the inlet pressure is above 15 PSIG at a velocity of 2.0 M/sec, the channel is too thin.

For cell suspensions having an optical density (OD) of 2 to 500, and a path length of 25 to 40 inches, start with a channel height between 0.7 to 1.0 mm. If the inlet pressure is below 5 PSIG at a velocity of 2.0 M/sec, the channel is too high.

Shear at the surface of the membrane is critical in minimizing gel layer formation, but excess shear is deleterious in at least three key aspects: first, it increases energy consumption costs; second, excess shear and the resulting pressure has been demonstrated to interfere with separations which appear to be based on diffusion at the membrane surface; and third, shear can result in damage to cells and impairment of the bioactivity of certain compounds. It is apparent that the benefits of shear are readily observed within a specific range for each process and that shear rates outside that range are highly destructive.

Before progressing in the explication of the optimization process, it must be pointed out that the shear stability of the substances in solution or suspension is a key element in shear optimization. Only through accurately calculating and charting the specific shear rates utilized during optimization can the true benefits of shear optimization become apparent. In concentration processes, it is graphically clear that the higher the shear, the higher the membrane flux, with two striking observations.

First, there is a minimum shear value that minimizes the gel-layer formation. This minimum shear can be best demonstrated for any specific solution by first running the device at an excessively high shear rate and then systematically lowering the shear incrementally until the resultant flux decay of each incremental reduction in shear is disproportional to the reduction in shear. Given the repeated observation during cross-flow concentration applications that increasing the shear increases the flux, the maximum flux for solutions is clearly governed by the law of diminishing returns, where at some point increases in shear provide lower increases in flux.

For concentration applications, it can be stated that there is a minimum shear required to keep the membrane clean through minimizing the gel-layer formation, as well as a maximum shear which is determined by the cost of energy required to marginally increase flux.

For separation applications it can be stated that there is a minimum shear required to minimize the gel-layer formation and allow the passage of a target substance, as well as a maximum shear that interferes with the passage of a target substance, even though the higher shear results in higher water flux rates.

Furthermore, it is possible to develop processes based on channel velocity, given that most cross-flow end users tend to work with a single channel height based on past experiences, and the predominance of cross-flow modules that are only available in a single channel height.

When working with a single device of uniform height, shear is directly proportional to channel velocity for the same solution. In concentration applications, the end user should install a flow meter on the permeate port and record the maximum flux obtained at reasonable cross-flow velocities between 1 and 4 M/sec for devices with channel heights between 0.5 mm and 1.0 mm. In separation applications, the end user should assay the passage of the target material(s) at cross-flow velocities between 0.5 and 2.5 M/sec for devices with channel heights between 0.5 mm and 1.5 mm The optimization of transmembrane pressure (TMP) can only be performed after the appropriate tangential velocity has been determined. Transmembrane pressure is calculated as TMP=(inlet pressure+outlet pressure)/2−permeate pressure. It is imperative that the tangential velocity (flow rate) be monitored during the optimization of transmembrane pressure, since increasing the pressure normally decreases the output of most pumps due to slippage. The objective of the optimization of transmembrane pressure is to define the correlation of transmembrane pressure to permeate flow rate. The normal relationship is a traditional bell curve. A graph of transmembrane pressure versus permeate flow rate should resemble a bell curve. Increases in transmembrane pressure cause increases in the permeate rate until a maximum is reached, and thereafter further increases in transmembrane pressure result in decreases in the permeate rate. The reason for this result is that the decreasing flow rate, resulting from higher transmembrane pressures, is the result of gel layer and/or membrane compression.

The procedure is set out below:
(1) Operate the system in total recycle mode at the optimum tangential velocity for sufficient time, typically fifteen minutes, for any gel layer to accumulate.
(2) Measure the permeate rate. This is the Base Rate.
(3) Increase the transmembrane pressure by 3 PSIG and measure the permeate rate immediately and after five minutes at the new transmembrane pressure. Compare the permeate rates to the base rate. If the rates have increased go to Step 4. If the rate decreases go to step 5.
(4) Repeat steps 2 and 3 until the permeate rate no longer increases during each step or does not hold that increase for five minutes.
(5) The optimum transmembrane pressure is the last pressure reading where the increase in pressure result in an increase in permeate rate.

In separation applications, the end user should assay the passage of the target material(s) at TMP's between 2 and 15 PSIG where the cross-flow velocity is optimized between 0.5 and 2.5 M/sec for devices with channel heights between 0.5 mm and 1.5 mm.

Selecting and optimizing the channel length has been totally impractical if not an impossible task until the advent of the stacked cross-flow filtration units as described herein. The inherent difficulty of optimizing the channel length in prior art devices has been three-fold: first, the devices such as spirals were designed to maximize membrane utilization based on the width that membranes could be cast rather than any other factor; second, increases in channel length for devices such as cassettes resulted in enormous increases in pressure drop due to the predetermined channel geometry imposed by the retentate screen; and third, plate and frame devices, such as for example Pleidae by Rhodia, France, use fixed molded plates which are manufactured in a single length and cannot be changed without manufacturing a new mold.

The present invention eliminates these prior art restrictions by providing the ability to select the channel length by utilization of an infinitely variable retentate sheet that is cut to length from an appropriately manufactured film, selected from a variety of standard or starting point thicknesses. Likewise, the membrane sheets and permeate sheets are cut to matching lengths and laminated into a stacked cassette.

There undoubtedly are many ways of selecting the optimum membrane for any given process, yet it appears the most reliable method of using membranes is to consider the manufacturer's specified pore size as a theoretical starting point which then is modified by the solution and the operating conditions. As a result of numerous trials, a practical parameter has been determined and termed the coefficient of rejection.

Coefficient of Rejection (CRV)

Membranes have a rejection characteristic (value) that is first order and is defined by the size, charge and shape of the pore. For simplicity the CRV, coefficient of rejection value, is the stated pore size provided by the manufacturer. In purifying a product of interest the CRV of a membrane is more important for separation applications as compared to concentration applications. The rules below specifically relate to separation applications. These effects will vary in concentration applications.

The CRV of a membrane is subject to the velocity of the tangential flow operation. Empirical evidence suggests that the neutral point of any membrane can occur in two zones, the first zone being the point at which the transmembrane pressure and/or shear compress the gel layer and the CRV increases, and the second zone occurring where the TMP and velocity minimize the shear and the CRV decreases. The neutral point (NP) is defined as the point where a membrane freely passes particles 0.5 times the stated pore size, NP=0.5 (Pore Size).

Therefore:
the effective CRV of a typical micro porous membrane is greater than the pore size, for velocities greater than 1.5 M/sec and less than 3.0 M/sec.; and
the effective CRV of a typical ultrafiltration membrane is greater than the pore size, for velocities greater than 1.5 and less than 3.0 M/sec.

Example: A 0.3µ particle may freely pass a 0.45µ polymeric membrane when the velocity is between 1.5 and 4.0 M/sec but not for velocities between 0.5 and 1.5 M/sec or 4.5 and 12 M/sec.

Example: A 45,000 MW protein may freely pass a 0.2µ membrane for velocities of 0 to 1.0 M/sec but be significantly retained when the velocity is increased above 1.5 M/sec. In the same experiment, it was documented that protein passage was above 90% for velocities between 0.8 and 1.5 M/sec and 25% for a velocity of 2.0 M/sec. Additionally, this same protein had 65% membrane transmission through a 100,000 MW membrane at velocity of 1.0 M/sec.

Further,
the CRV of a membrane is proportional to the molarity of the solution;
the greater the solute concentration, the greater the CRV; and
the lower the solute concentration, the smaller the CRV.

Thus, a membrane may have a stated pore size of 500,000 MW but will retain proteins of 110,000 MW in cell suspension with an OD over 100 and pass the same 110,000 MW protein when the OD is less than 50.

The process can be developed and optimized by empirical testing of undiluted and/or diluted volumes of starting source material to measure the percent of target molecule passed into the permeate fluid. Two testing methodologies can be employed including:

1) Concentrate the undiluted and/or diluted material as much as possible, from 1 to 10× for example, collect and assay samples of the retentate fluid and the permeate fluid simultaneously collected at various points in the concentration process such as start, 2×, 3×, 5×, 7× and 10×, divide the assayed level of target substance measured in the permeate fluid by the assayed level of target substance in the retentate sample that was taken at the same point in time and multiply by 100 in order to express the result as percent passage of the target material.

2) Continuously diafiltering the undiluted and/or diluted material against multiple volumes, from 1 to 10× for example, collect and assay samples of the retentate fluid and the permeate fluid simultaneously collected at various points in the diafiltration process such as start, 2×, 3×, 5×, 7× and 10×, divide the assayed level of target substance measured in the permeate fluid by the assayed level of target substance in the retentate sample that was taken at the same point in time and multiply by 100 in order to express the result as percent passage of the target material.

The data from these two processes will indicate several key factors which will provide a total isolation process as described herein:

a) The appropriate dilution of the starting material that results in good passage of the desired product away from the starting material.
b) The number of diafiltration volumes necessary to achieve an acceptable yield.
c) The degree of concentration to which the starting material can be concentrated.
d) The membrane performance of the tested membranes at the operating conditions utilized in the testing.
e) Optimization of the membrane performance.

A succinct description of the process would be to start the isolation of a desirable product from a viscous mixture by diluting the starting mixture the minimum amount necessary to effect good passage of the target substance through a separating membrane, followed by continually diafiltering the diluted material on said separating membrane with sufficient diafiltration volumes to achieve the desired yield, then to concentrate the diluted mixture on a second membrane device to recover the diluent for recycling while simultaneously concentrating the permeate fluid, containing the product of interest that was in the mixture, on the separating membrane, such that the product is concentrated. Then the product-free permeate is utilized and recycled as the diafiltration buffer such that at the end of the process, the product has been isolated from the viscous mixture and concentrated into a smaller volume, i.e. less than the volume of the undiluted starting material. Further any remaining starting material is returned to the initial undiluted viscous volume, or a lower volume, and no buffers where consumed other than the initial volumes utilized to start the process.

Another way to understand the invention is to look at how the fluid flows through the various steps mathematically:

The terminal retentate flow (TRF), in liters per hour, for the starting material concentration step (SMCS) is approximately equal to the starting volume (SV) of the starting material, in liters, divided by the desired processing time (DPT), hours. TRF (LPH)=SV(L)/DPT (h)

In preferred embodiments of the apparatus, the terminal retentate flow derived from the starting material concentration step (SMCS) can be changed to a fraction of the starting volume (SV) flow rate by decreasing the volume of starting material in order to lower the waste stream or to concentrate the remaining dry matter in the starting volume (SV) as this fluid stream may be a valuable by-product. One such example would be to utilize the invention to isolate one or more proteins and/or carbohydrates from a plant material such as soy, potato, tobacco and milk where the starting material less the protein or carbohydrate had residual value as a bulk protein or additive to a third product such as soy flour, milk powder, and fish feeds etc. The reduced volume would lower the cost of either drying or transporting the liquid stream.

The feed flow rate (FF), in liters per hour, into the separating filter apparatus (SFA) is equal to the terminal retentate flow rate (TRF) where no concentration of the starting volume is desired. FF (LPH)=TRF (LPH)=SV(L)/DPT (h)

If for example the terminal retentate flow rate (TRF), in liters per hour, is to be one-half (½) of the starting solution flow rate (PF) when there is no dilution of the starting solution, then the equation is simply modified. FF (LPH)=PF (LPH)=2×RF (LPH)=0.5×(SV(L)/DPT (h))

Further, the feed flow rate (FF), in liters per hour, into the separating filter apparatus (SFA) is equal to the sum of the diluting fluid flow rate (DF) plus the product flow rate (PF). FF (LPH)=DF (LPH)+PF (LPH)

The retentate fluid flow (RFF), liters per hour, from the separating filter apparatus (SFA) into the starting material concentration step (SMCS) is equal to the feed flow rate (FF) when the feed flow rate is neither diluted or concentrated by the separating filter apparatus (SFA).

The diluting fluid flow rate (DF) is equal to the desired initial dilution for the product flow rate. If for example, it was determined that the product of interest could be separated when the starting material was diluted with an equal volume of buffer than the equation would be DF=PF wherein we could say that FF (LPH)=2×(SV(L)/DPT (h)).

If for example, it was determined that the product of interest could be separated when the starting material was diluted with two equal volumes of buffer than the equation would be DF=2×PF wherein FF=3×PF=3×(SV/DPT).

If for example, it was determined that the product of interest could be separated when the starting material was first concentrated in half before entering the separating filter apparatus (SFA) than the equation would be FF=0.5×PF.

If for example, the starting volume (SV) was to be concentrated in half within the separating filter apparatus (SFA) before initiating the diafiltration fluid flow than the equation would be TRF=0.5×PF.

The permeate fluid from the starting material concentration apparatus (PCA) replaces the diluting fluid flow rate (DF) that is utilized to dilute the starting volume as necessary. The equation for this relationship is PCA=DF.

The flow rate of diafiltration buffer (DFB) into the separating filter apparatus (SFA) is determined by the number of diafiltration volumes necessary to pass the target molecule into the permeate stream of the separating filter apparatus (SFA) in order to recover the desired yield of the target molecule. In the case where the diluting flow rate, expressed as DF, resulted in a process where the target substance passed freely into the permeate stream than the following table can be utilized to determine the yield of the target substance based on the number of diafiltration volumes.

Solute Recovery vs. Volume Replacement

| Volume Replacement | Recovery of Target Molecule in the Permeate Fluid i.e. when passage is unrestricted, 0% rejection |
|---|---|
| 0 | 0 |
| 1 | 50% |
| 2 | 75% |
| 3 | 87.5% |
| 5 | 96.9% |
| 7 | 98.7% |
| 10 | 99.8% |

In the case where the feed flow rate (FF) is to undergo diafiltration without being concentrated or diluted in the separating filter apparatus (SFA) than the feed flow rate will equal the retentate fluid flow (RFF) to the starting material concentration step (SMCS) and the permeate rate (PSA) of the separating filter apparatus is equal to the flow rate of diafiltration buffer (DFB) into the separating filter apparatus (SFA).

If for example, the process is determined to require a five (5) fold diafiltration of the feed flow rate (FF) in order to obtain a yield of 96.9%, as shown in the table, than the equation can be expressed as DFB=5×FF.

The permeate flow rate of the product concentration apparatus (PCA) needs to replace the permeate fluid discharged from the separating filter apparatus (SFA) as permeate flow rate of the separating filter apparatus is equal to the diafiltration buffer (DFB) flow rate such that the equation is PCA=DFB.

In preferred embodiments of the apparatus, it maybe advantageous to intermittently harvest the concentrated product from the product reservoir to avoid prolonged exposure to the shear forces of the concentrating membrane apparatus or simply to avoid product degradation over time as a result of varied biological and/or chemical effects.

Figure 1:
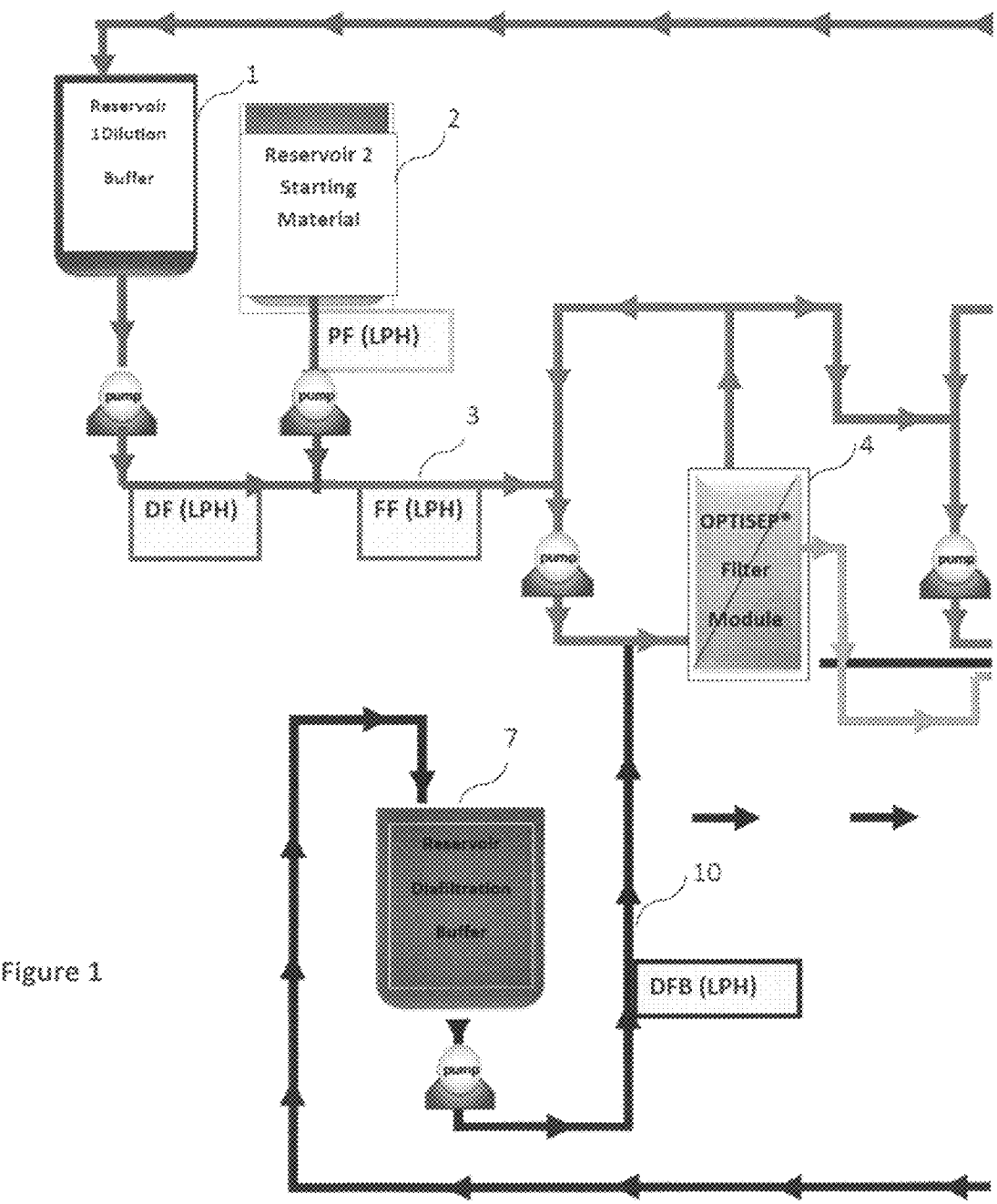
FIG. 1 shows a general scheme of an isolation system according to one embodiment of the invention, using a cross-flow filtration based apparatus FIG. 2 A shows stacking of permeate and retentate sheets in the cross-flow filter of the present invention; B shows the sheet members P/F/P according to another embodiment of the invention; and C shows plan view of retentate sheet of the present invention
Figure 1:
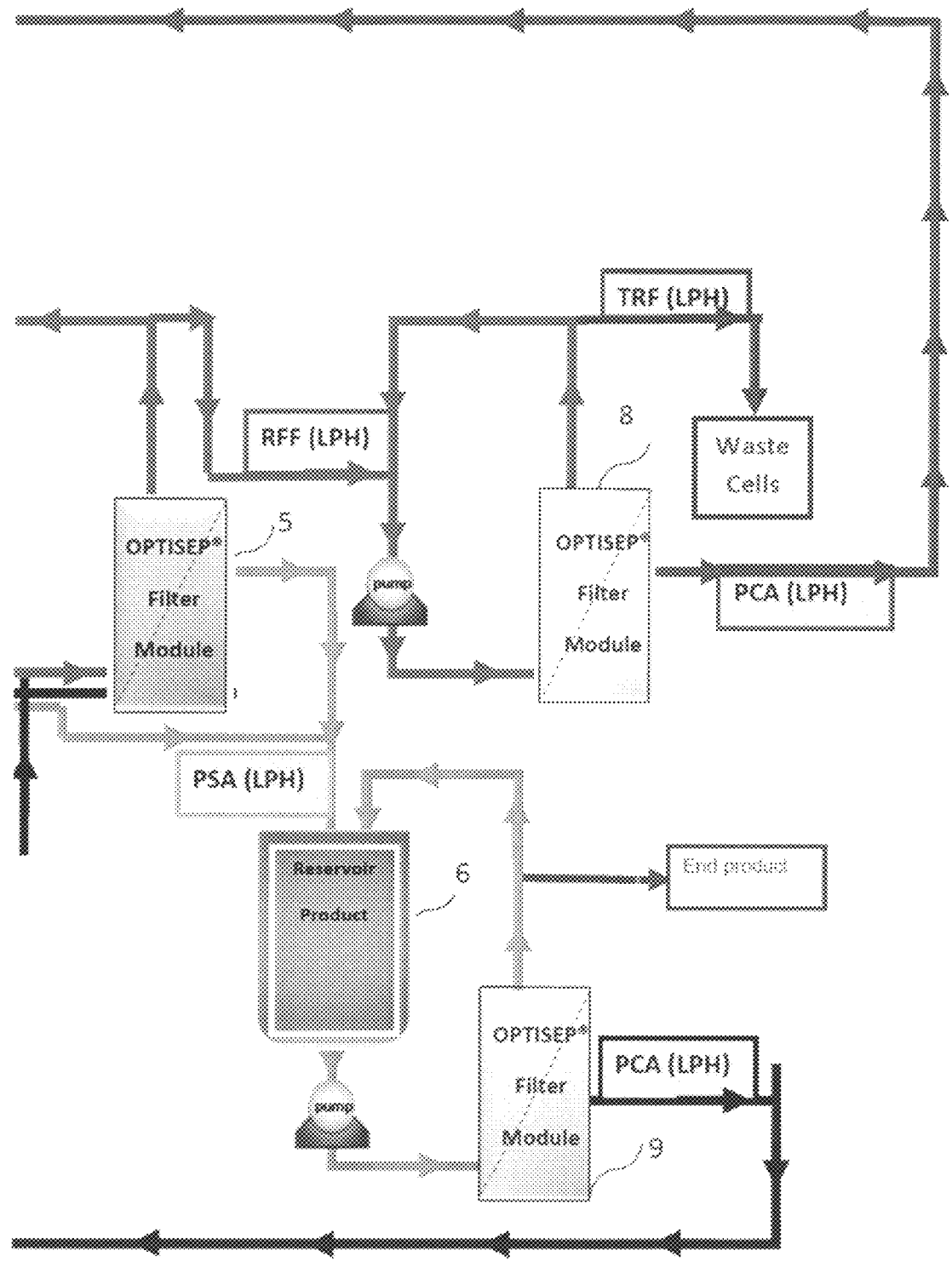

FIG. 1 shows an arrangement of reservoirs and cross-flow filtration units that is representative of one embodiment, understanding that a system may include from one to multiple reservoirs and cross-flow filtration units, the present system comprising:

A first reservoir 1 constructed and arranged for holding a diluent solution, and for selectively flowing liquid into and out of said first reservoir;

A second reservoir 2 constructed and arranged for holding a viscous starting source material, and for selectively flowing liquid into and out of said second reservoir, the second reservoir preferably is a cell culture reservoir such as a fermentor or culture bag; wherein the first and second reservoir are communicatively connected to a channel 3 for delivering components of the first and second reservoir and combining therein for delivery to at least one cross-flow filtration unit positioned downstream of the combining channel;

A first cross-flow filtration apparatus 4 for separating liquids into permeate and retentate streams, provided with means for flowing liquid in and permeate and retentate streams out of said first cross-flow filtration apparatus, wherein the permeate includes at least the target of choice and can be directed to a end product reservoir 6 and wherein the retentate comprises cell mass and/or culture material for movement downstream or recirculation into the first cross-flow filtration unit;

A second cross-flow filtration apparatus 5 communicatively connected to the first cross-flow filtration unit and retentate stream leaving therefrom, wherein the second cross-flow filtration unit is used for separating the retentate stream into permeate and retentate streams and provided with means for flowing liquid in and permeate and retentate streams out of said second cross-flow filtration apparatus, wherein the permeate includes at least the target of choice and can be directed to the end product reservoir 6 and wherein the retentate comprises cell mass and/or culture material for movement downstream or recirculation into the second cross-flow filtration unit;

A third reservoir 7 constructed and arranged for holding a diafiltration buffer, and for selectively flowing liquid into and out of said third reservoir; wherein the buffer is deliverable, though a channel system 10, to the first and second cross-flow filtration units and for mixing with the input stream therein;

A third cross-flow filtration apparatus 8 for separating retentate stream from the second cross-flow filtration apparatus into permeate and retentate streams, provided with means for flowing liquid in and permeate and retentate streams out of said third cross-flow filtration apparatus, wherein the third cross-flow filtration unit is communicatively connected to the retentate stream of the first and/or second cross-flow filtration unit; wherein the dilution buffer is removed via the permeate stream for optional recirculation into dilution buffer reservoir 1 and the retentate stream which includes waste cells can be optionally used for multiple purposes including further separation of additional target molecules or used in feed products for animals, both terrestrial and aquatic.

The end product reservoir 6 constructed and arranged for holding the isolated end product, and for selectively flowing liquid into and out of said end product reservoir; wherein the end product is removed directly from the end product reservoir or in the alternative directed through a separation cross-flow filtration unit 9 for separation of end product from at least the diafiltration buffering solution, wherein the diafiltration buffering solution can be directed to the buffer reservoir 7 for reuse in the system.

The system further comprises conduit, valve and pump means constructed and arranged to move liquid and slurries from different reservoirs to cross-flow filters. In preferred embodiments of the apparatus, the reservoirs are provided with thermal jackets to maintain appropriate process temperatures.

An illustrative example is provided using the system of OPTISEP® filtration modules for processing *Pichia pastoris*. The present example can be used to separate expressed proteins from high cell density *P. pastoris* cell culture, wherein the starting concentration of 50% solids is able to provide a recovery of 95%+.

The process comprises diluting the *Pichia* so that it is readily filtered (step 1), then filtering the diluted material in a first OPTISEP® filter module via diafiltration so as to separate the product from the feed stock (step 2), while simultaneously: a) concentrating the permeate on a second OPTISEP® filter module which both concentrates the product and recycles the diafiltration buffer (step 3) and b) concentrating the retentate of the first OPTISEP® filter module with a third OPTISEP® filter module recovering the diluent and returning the feed stock to its original volume or less (step 4).

Figure 3:
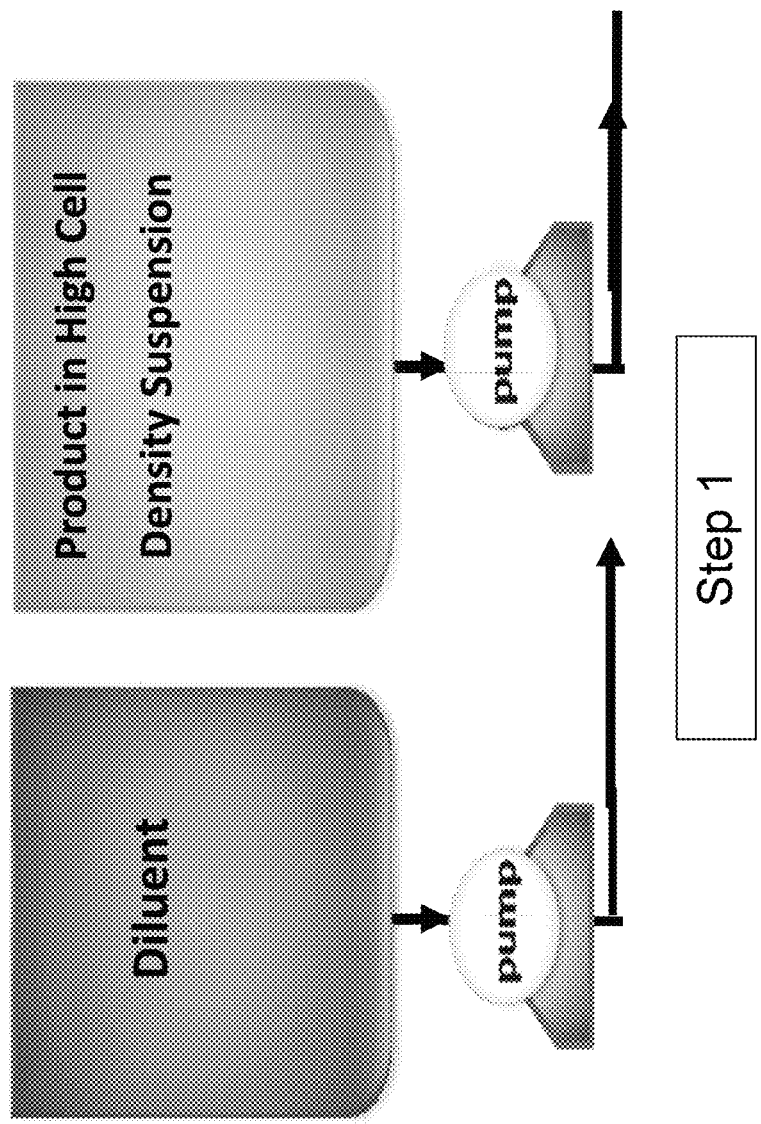
FIG. 3 shows the system components for diluting the source material comprising the desired product.

Typical *P. pastoris* fermentations can reach a wet cell weight of 50 to 60%. At these high solid concentrations, the culture typically must be diluted to permit effective passage during filtration. The dilution step 1 is depicted in FIG. 3 and includes the following observations and or parameters:

- The cell culture is diluted to a predetermined concentration with diluent.
- The flow rate of cell culture fluid into the diluent is equal to the volume of cell culture fluid divided by the desired processing time.
- Increasing the amount of diluent increases the effective separation of product from the cell suspension.
- Increasing the amount of diluent increases the flux rate of the membrane.
- Increasing the amount of diluent decreases the operating pressure.
- Increasing the amount of diluent increases the total volume of liquid to be processed.

Figure 4:
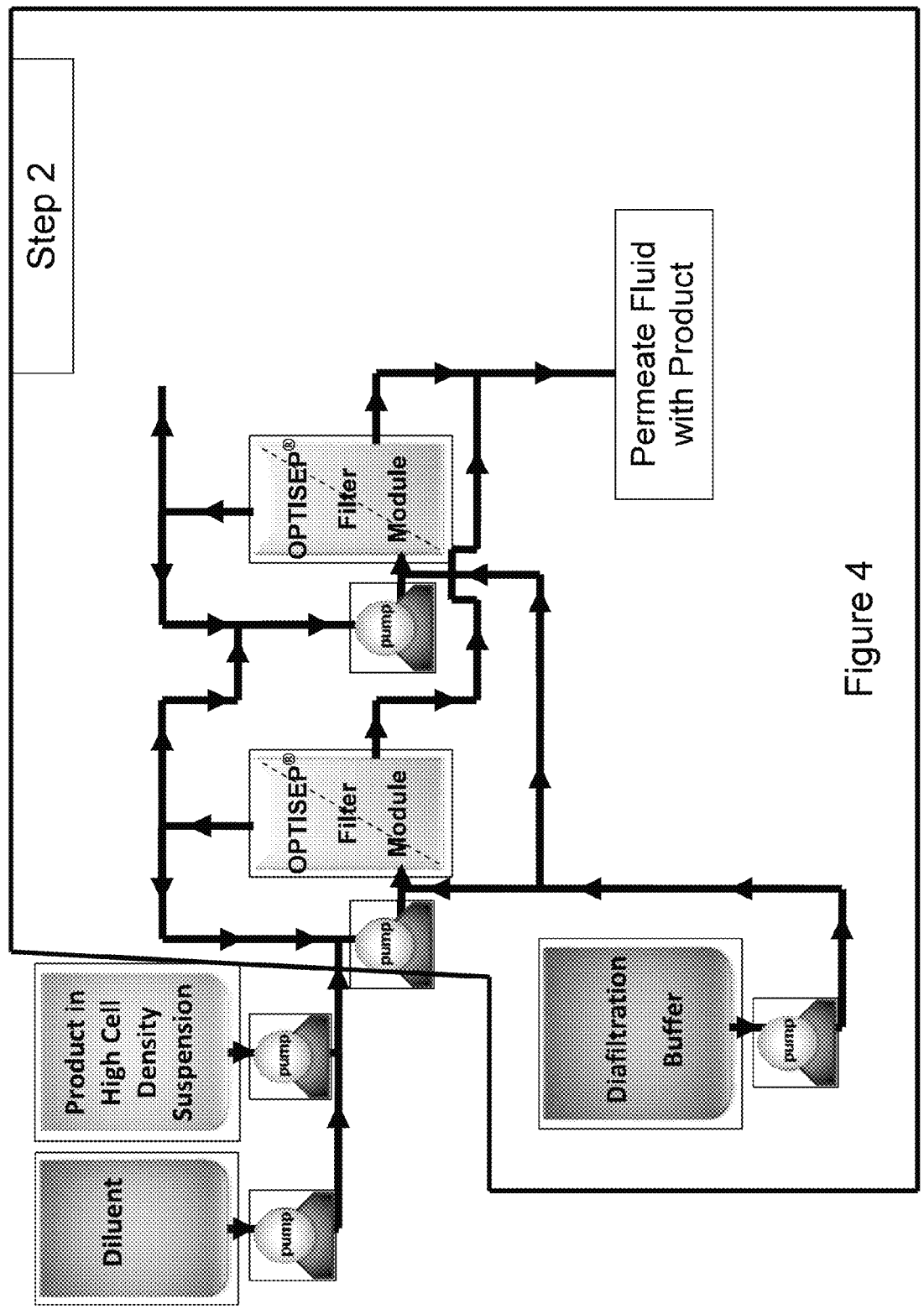
FIG. 4 shows the system components for moving the diluted source material through a cross-flow filtration stack and the addition of buffer to the cross-flow filtration wherein the permeate from the first and second cross-flow filtration stacks is moved to a product reservoir.

Step 2, once the culture is diluted; the cells are separated from the product in solution using an OPTISEP filter module with a microfiltration (MF) membrane. In this process, the product passes through the MF membrane into the MF permeate by continuous diafiltration, as labeled in step 2 (FIG. 4) the cells remain in the recirculation loop, i.e. the retentate fluid. The MF membrane capacity is increased by adding more membrane area to the filter holder and/or more recirculation loops. The attached depiction of FIG. 4 shows two (2) recirculation loops in series with one filter holder in each loop. Because the diafiltration is a steady state diafiltration, the volume entering the loop (i.e. the feed rate) is equal to the volume leaving the loop (i.e. the bleed rate) and the volume of permeate leaving the loop (i.e. permeate rate) is equal to the volume of diafiltration buffer entering the system (i.e. the diafiltration rate.) Therefore, the concentrations of the cells entering, leaving, and inside the recirculation loop are constant at the optimal concentration set in the dilution step (step 1). The concentrations of the molecules that pass through the membrane such as the product are reduced. The source of the diafiltration buffer is described in the third step. The concentration step 2 includes the following observations and/or parameters:

- The flow rate into the MF stage is equal the flow rate out of the MF stage
- The permeate rate out of the MF stage equals the flow rate of diafiltration buffer into the MF stage.
- Increasing the diafiltration factor will increase the product yield.

Figure 5:
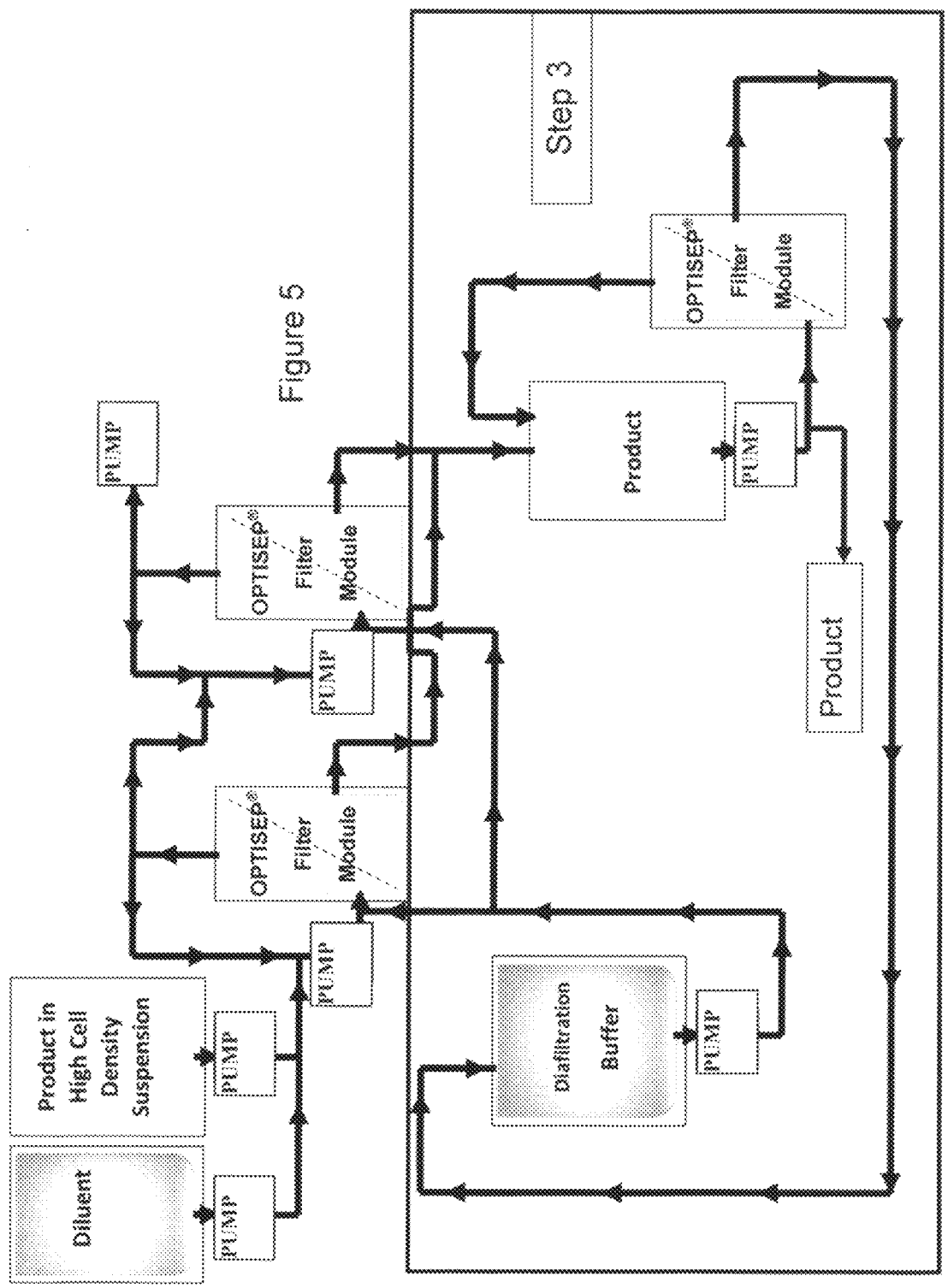
FIG. 5 shows the system components for further concentration of the permeate in the product reservoir wherein the buffer in the permeate is separated and moved back to the buffer reservoir for reuse.

The third step (Step 3, FIG. 5) is the concentration of the product derived from the MF permeate fluid as well as generating the diafiltration buffer. Utilizing a second OPTISEP filter module containing an ultrafiltration (UF) membrane, the permeate fluid of the MF membrane containing the product protein is concentrated. The product is concentrated in the retentate of this filter as depicted in FIG. 5. The UF permeate is recycled back to step 2 as the diafiltration buffer. This recycling dramatically lowers the waste produced from the system and decreases the operating expenses through the virtual elimination of buffers normally required for diafiltration. The concentration of the product includes the observations and/or parameters:

- MF permeate containing the product is concentrated.
- The rate of concentration is equal to the rate of the diafiltration of step 2.
- Product can be continually harvested from the product retention loop or the product vessel if desired.

Figure 6:
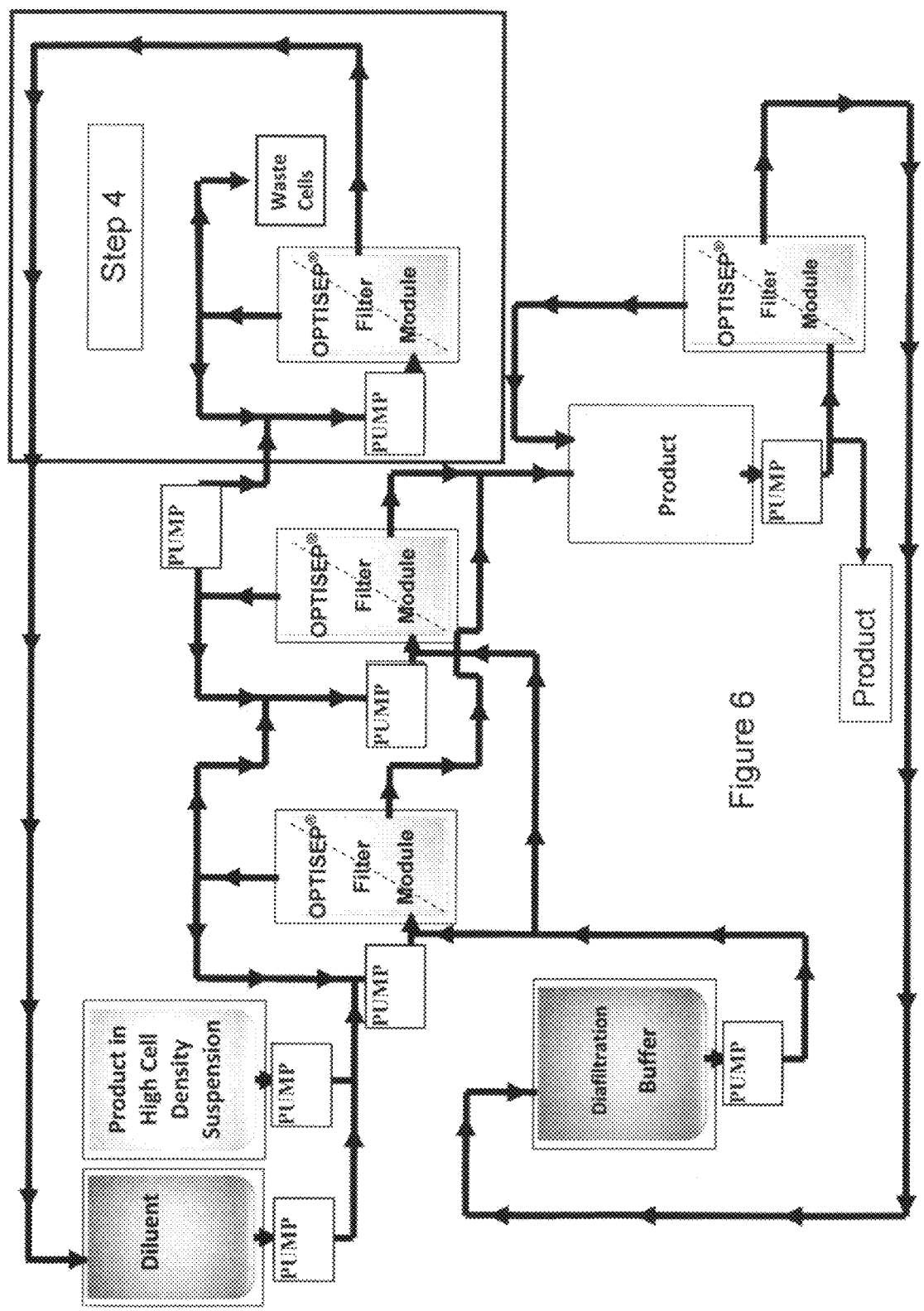
FIG. 6 show the recapturing of the diluent in the retentate and the separation of waste cells.

The fourth and final step is the concentration of the cells back to their original concentration or a higher concentration using the third OPTISEP filter module with a UF membrane, step 4 (FIG. 6). By concentrating the cells, the volume of cell waste is decreased. The recycle of the permeate dramatically lowers the waste produced from the system and decreases the operating expenses through the virtual elimination of the diluent needed to lower the concentration of the original fermentation broth. In certain situations this step could be accomplished with an MF filter such that the number of diafiltration required in step 2 would be reduced and the permeate flow paths would be altered slightly from the attached slides. The concentration of the cells back to the original concentration includes the following observations and/or parameters:

- The diluted cell broth is concentrated back to the original cell concentration or greater.
- The permeate fluid of the concentration is recycled back to be reused as a diluent.
- The final volume of cell paste can be less than the volume of the fermentor.
- The final volume of cell paste can be chemically and/or heat treated in line for discharge.

One advantage of separating the overall process into these 4 distinct unit operations is that each unit operation can be studied, understood, and optimized independently. Then the optimized parameters can be implemented when designing the large scale design.

Figure 7:
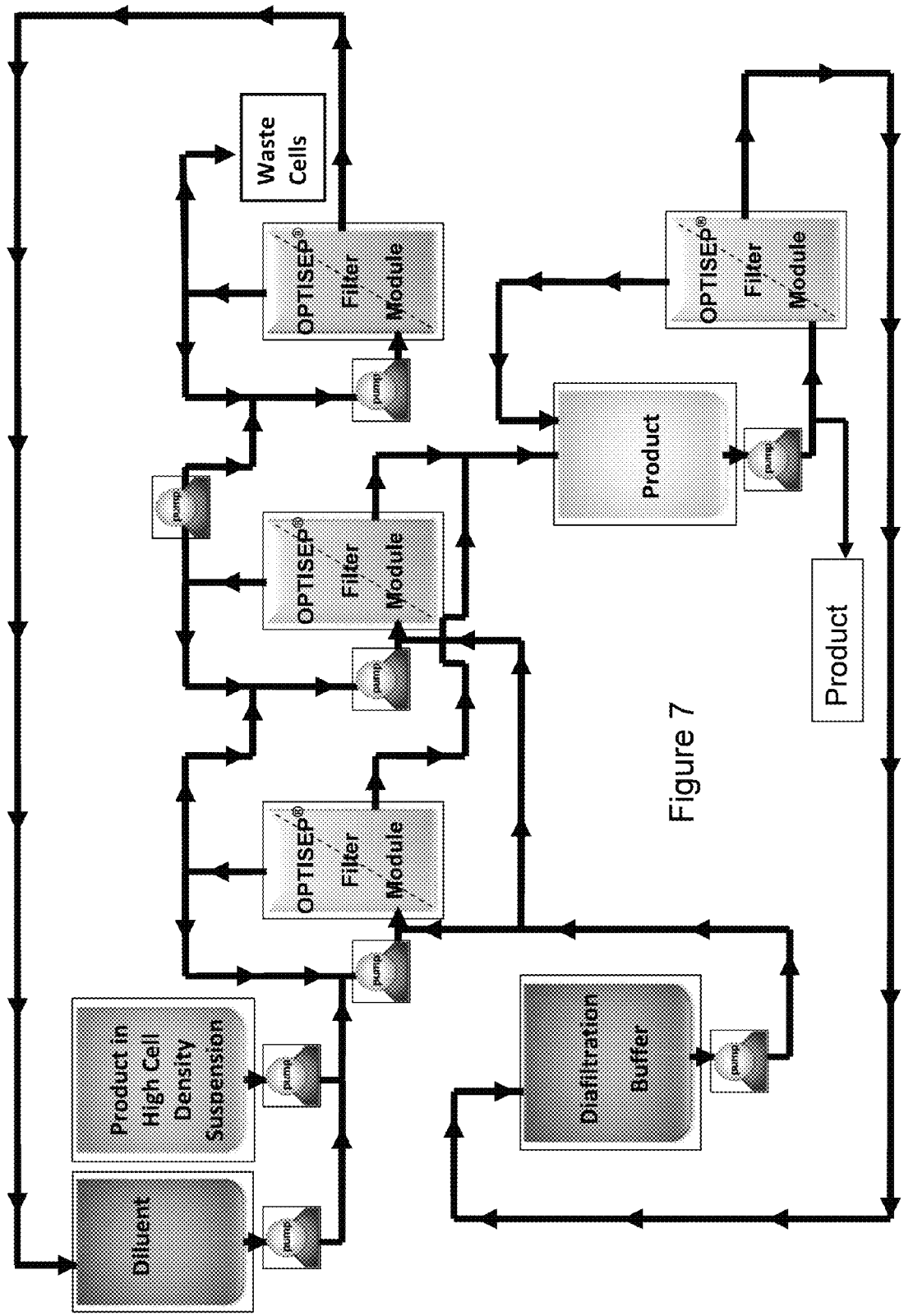
FIG. 7 shows the full components of the system as described in FIGS. 3, 4, 5 and 6.
Figure 8:
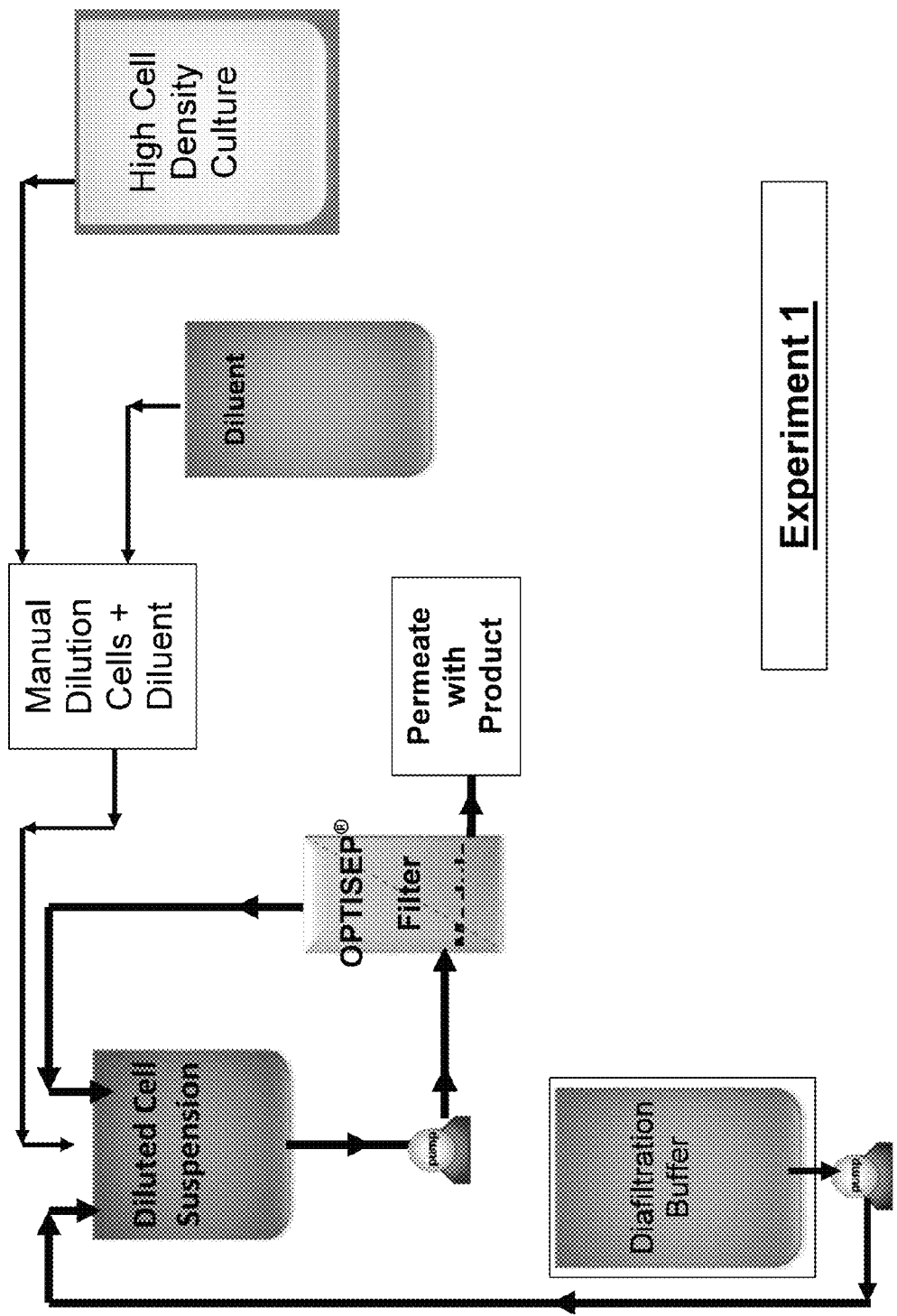
FIG. 8 shows the system for passage of the product away from the diluted cell suspension.
Figure 9:
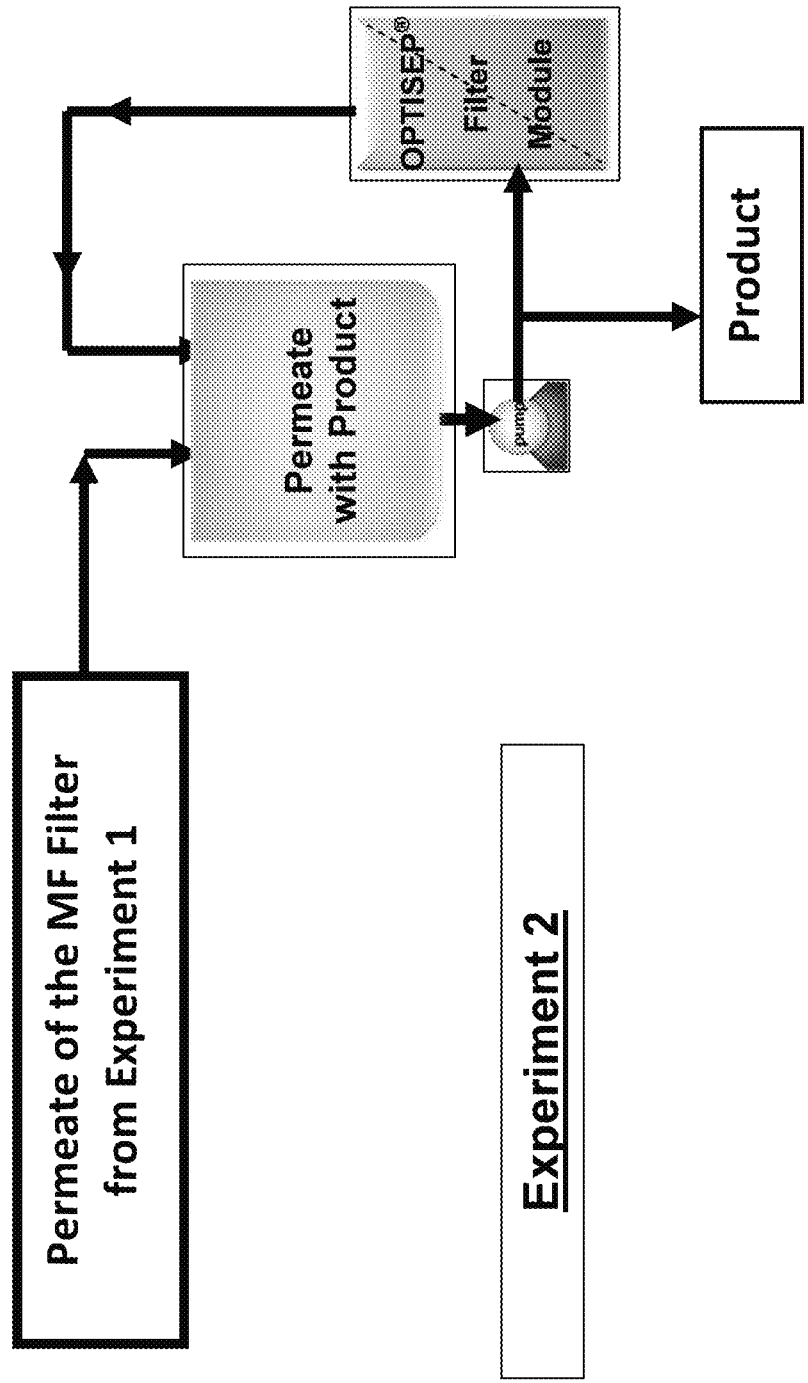
FIG. 9 shows the separation of product from the cell suspension by constant diafiltration of the cells.
Figure 10:
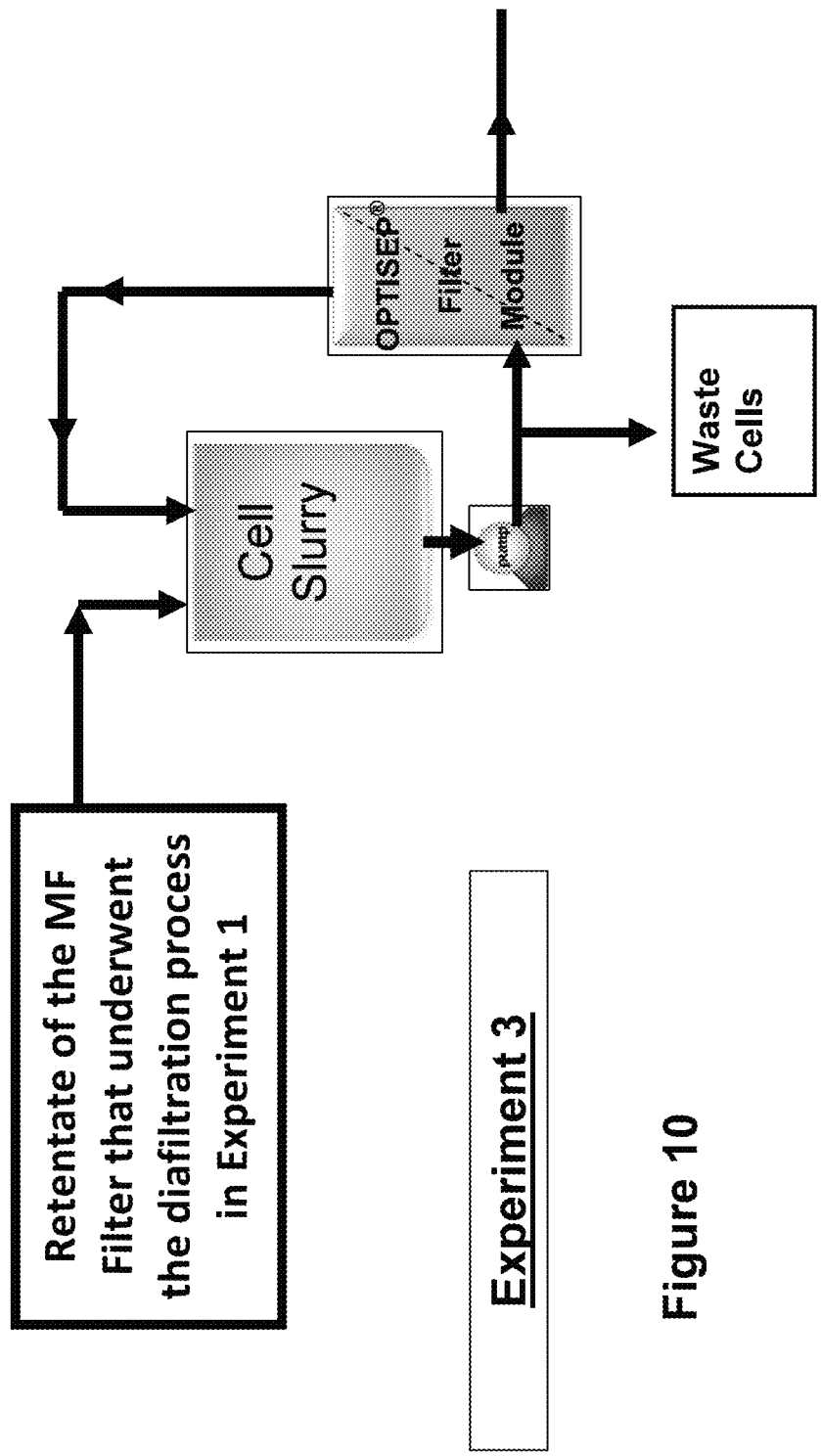
FIG. 10 shows the components required to concentrate diafiltered retentate of FIG. 8 to show the return of cell mass to original volume of undiluted cell mass.

FIG. 7 shows the entire process without the various visual keys.

Optimization of the process includes the following experiments as outlined in FIGS. 8, 9, 10 and 11 including;

Experiment 1

The purpose of experiment 1 is to demonstrate the passage of the product away from the diluted cell suspension. Experiment 1 is performed at various dilution rates to optimize product recovery, minimize the rate of dilution and maximize the membrane performance in liters per meter square per hour (LMH). The starting material is diluted in a batch mode using different levels of diluent to determine the appropriate dilution and the product is separated from the diluted starting material via constant volume diafiltration. The level of diafiltration is determined.

Experiment 2

The purpose of experiments 2 is to concentrate the permeate of experiment 1. The permeate of experiment 1 contains the product which was separated from the cells by constant volume diafiltration of the cells. The permeate of the separation is concentrated in order to demonstrate recovery of the product and number of passes through MF for acceptable product concentration.

Experiment 3

The purpose of experiments 3 is to concentrate the diafiltered retentate of experiment 1 in order to demonstrate the ability to return the cell mass to the original undiluted volume or less. In other words the purpose of experiment 3 is to show the feasibility of reducing the volume of the process waste stream as well as the ability to recover the diluent. The diluted cellular material is concentrated to the original starting volume or less and number of passes through MF for acceptable concentration.

Another embodiment for optimization comprises performing experiments 1, 2 and 3 utilizing three (3) different filtration steps (MF, UF of the MF permeate, and UF of cells); followed by a experiment 4 (FIG. 11) which is the simultaneous operation of the MF separation and the UF concentration of the MF permeate fluid Experiment 4

The purpose of Experiment 4 is the separation of the product from the cells by constant volume diafiltration while simultaneously concentrating the product such that the product is concentrated and the permeate of the product concentration is recycled as the diafiltration buffer. The diluted starting material is simultaneously separated and the product harvested via one MF and one UF membrane working simultaneously.

What is claimed is:

1. A method to isolate carbohydrates from a viscous plant material, said process comprising:
   contacting the viscous plant material with a diluent in an amount sufficient to reduce the viscosity of the viscous plant material and form a continuous stream of diluted plant material, wherein the diluent is contained in a diluent vessel and the viscous plant material is contained in a starting source material vessel;
   flowing the diluted plant material into a recirculation loop of a first cross-flow filter apparatus;
   diafiltering the diluted plant material with sufficient diafiltration buffer retained in a buffer reservoir so as to recover the desired yield of the carbohydrates by passing said carbohydrates into the first permeate fluid;
   flowing the first permeate fluid containing the carbohydrates to an end product vessel;
   flowing out the first retentate solution from the recirculating liquid of the first cross-flow filter into a second cross-flow filter unit, wherein the flow rate of the first retentate solution is at the same flow rate as the diluted plant material being fed into the recirculation loop of the first cross-flow filter apparatus;
   diafiltering the flow of retentate into the second cross-flow filter unit with sufficient diafiltration buffer retained in the buffer reservoir so as to recover the desired yield of the carbohydrates by passing said carbohydrates into the second permeate fluid;
   flowing the second permeate fluid containing the target substance to the end product vessel;
   concentrating the first and second retentate fluid by flowing same to a third cross-flow filter apparatus communicatively connected with the second cross-flow filter unit, wherein the volume of the third retentate fluid is reduced to the approximate volume of the undiluted plant material or less thereby forming a waste stream for further use;
   recirculating the third permeate fluid back to the diluent vessel for reuse;
   concentrating the first and second permeate fluid by flowing same to a fourth cross-flow filter apparatus communicatively connected to the end product vessel wherein the carbohydrates are concentrated and diafiltration buffer is removed in fourth permeate stream back to the buffer reservoir for reuse.

2. The method of claim 1, wherein the amount of buffer introduced into the buffer vessel is conserved and available for reuse.

3. The method of claim 1, wherein the diluent is returned to the diluent vessel while simultaneously concentrating the carbohydrates.

4. The method of claim 1, wherein the cross-flow filters comprises:
   a multilaminate array of sheet members of generally rectangular and generally planar shape with main top and bottom surfaces, wherein the sheet members include in sequence in the array a first retentate sheet, a first filter sheet, a permeate sheet, and second filter sheet, and a second retentate sheet, wherein each of the sheet members in the array has at least one inlet basin opening at one end thereof, and at least one outlet base opening at an opposite end thereof, with at least one permeate passage opening at longitudinal side margin portions of the sheet members;
   each of the first and second retentate sheets having at least one channel opening therein, wherein each channel opening extends longitudinally between the inlet and outlet basin openings of the sheets in the array and is open through the entire thickness of the retentate sheet, and with each of the first and second retentate sheets being bonded to an adjacent filter sheet about peripheral and side portions thereof, with their basin openings and permeate passage openings and register with one another, and arranged to permit flow of filtrate through the channel openings of the retentate sheet between the inlet and outlet basin openings to permit permeate flow through the filter sheet to the permeate sheet to the permeate passage openings; and
the cross-flow filters comprising a unitary article of interbonded sheet members.

5. The method of claim 4, wherein the first and second retentate sheets comprise an optimal channel height and an optimal channel length for optimal production yield.

6. The method of claim 1, wherein the plant material is soy, potato, or tobacco.

* * * * *